(12) United States Patent
Mitchell et al.

(10) Patent No.: US 9,914,742 B2
(45) Date of Patent: Mar. 13, 2018

(54) TETRA-HETEROARYL INDACENODITHIOPHENE-BASED POLYCYCLIC POLYMERS AND THEIR USE

(71) Applicant: Merck Patent GmbH, Darmstadt (DE)

(72) Inventors: William Mitchell, Chandler's Ford (GB); Mansoor D'Lavari, Bude (GB); Changsheng Wang, Durham (GB); David Sparrowe, Bournemouth (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/329,645

(22) PCT Filed: Jun. 26, 2015

(86) PCT No.: PCT/EP2015/001295
§ 371 (c)(1),
(2) Date: Jan. 27, 2017

(87) PCT Pub. No.: WO2016/015804
PCT Pub. Date: Feb. 4, 2016

(65) Prior Publication Data
US 2017/0210752 A1    Jul. 27, 2017

(30) Foreign Application Priority Data
Jul. 29, 2014  (EP) .................... 14002627

(51) Int. Cl.
| C07D 495/02 | (2006.01) |
| H01L 51/50 | (2006.01) |
| C07D 495/04 | (2006.01) |
| C08G 61/12 | (2006.01) |
| C08L 65/00 | (2006.01) |
| H01L 51/00 | (2006.01) |

(52) U.S. Cl.
CPC .......... *C07D 495/04* (2013.01); *C08G 61/12* (2013.01); *C08L 65/00* (2013.01); *H01L 51/0036* (2013.01); *C08G 2261/00* (2013.01)

(58) Field of Classification Search
CPC ............... C07D 495/02; H01L 51/50

USPC .................... 549/41; 313/504, 498
See application file for complete search history.

(56) References Cited

U.S. PATENT DOCUMENTS

| 9,287,504 | B2 | 3/2016 | Blouin et al. |
| 2013/0175481 | A1 | 7/2013 | Blouin et al. |
| 2014/0158949 | A1 | 6/2014 | Wang et al. |

FOREIGN PATENT DOCUMENTS

| EP | 2075274 A1 | 7/2009 |
| KR | 10-2014-0047812 A | 4/2014 |
| WO | 2012/003918 A1 | 1/2012 |
| WO | 2013/010614 A2 | 1/2013 |

OTHER PUBLICATIONS

International Search Report dated Aug. 14, 2015 issued in corresponding PCT/EP2015/001295 application (4 pages).
Written Opinion of the International Searching Authority dated Aug. 14, 2015 issued in corresponding PCT/EP2015/001295 application (7 pages).
English Abstract of KR 2014-0047812 A published Apr. 23, 2014.
Y. Sun et al., "High-Mobility Low-Bandgap Conjugated Copolymers Based on Indacenodithiophene and Thiadiazolo [3,4-c]Pyridine Units for Thin Film Transistor and Photovoltaic Applications", Journal of Materials Chemistry, vol. 21, No. 35 (2011) pp. 13247-13255.
C.C. Chueh et al., "Non-Halogenated Solvents for Environmentally Friendly Processing of High-Performance Bulk-Heterojunction Polymer Solar Cells", Energy & Environmental Science, vol. 6, No. 11 (2013) pp. 3241-3248.
Y.H. Kim et al., "Production of Heat Stable Novel Organic Semiconductor Compound for Preparing Photoactive Layer Used in Thin Film Solar Cell with Broad Absorption Area", Database CA [Online] Chemical Abstracts Service (Apr. 29, 2014) XP002742987.

*Primary Examiner* — Charanjit Aulakh
(74) *Attorney, Agent, or Firm* — Millen White Zelano and Branigan, PC; Csaba Henter

(57) ABSTRACT

The present invention relates compounds comprising a tetra-heteroaryl indacenodithiophene-based structural unit, the synthesis of such compounds as well as their use in organic electronic devices. The invention further relates to organic electronic devices comprising such compounds.

20 Claims, 1 Drawing Sheet

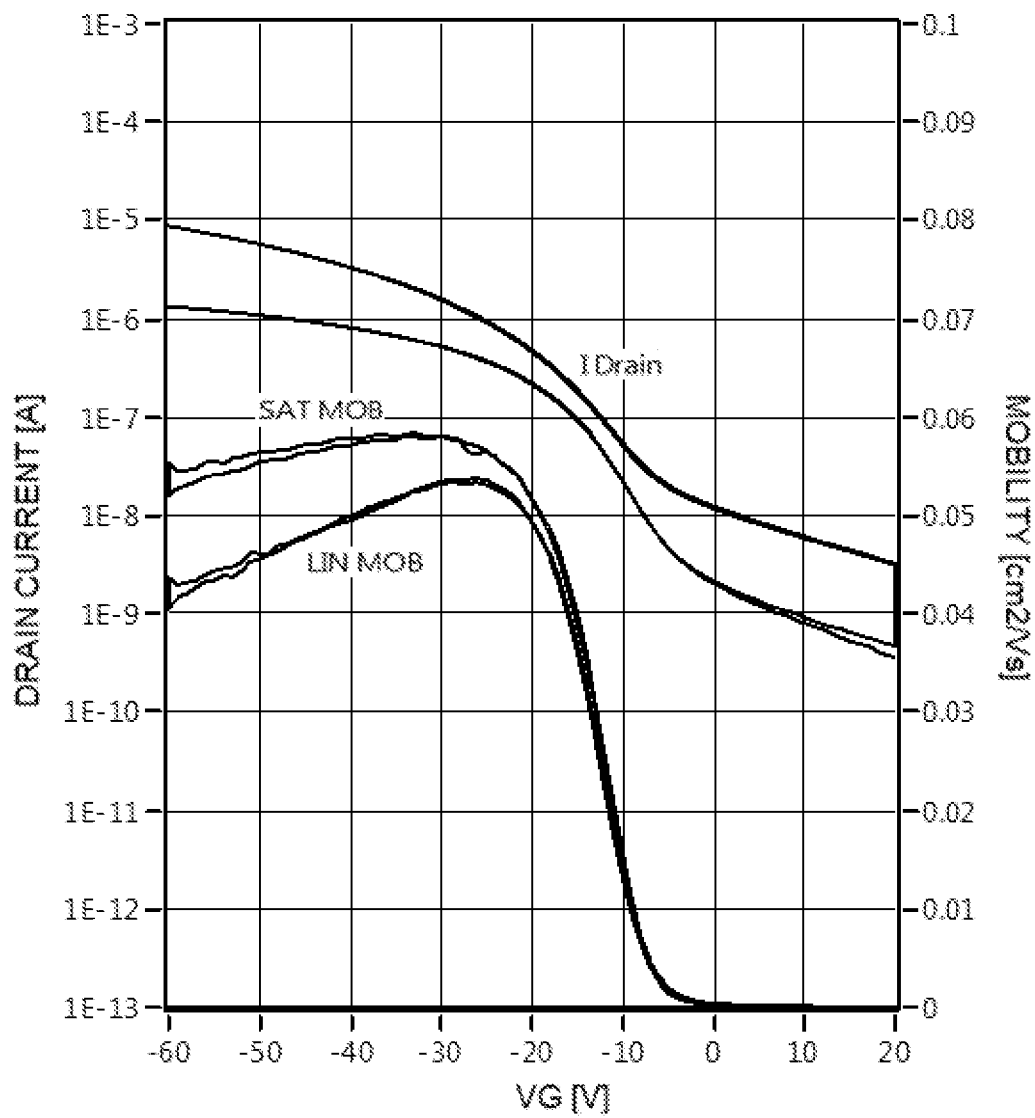

US 9,914,742 B2

TETRA-HETEROARYL INDACENODITHIOPHENE-BASED POLYCYCLIC POLYMERS AND THEIR USE

TECHNICAL FIELD

The present invention relates to compounds comprising a tetra-heteroaryl indacenodithiophene-based structural unit, the synthesis of such compounds as well as their use in organic electronic devices. The invention further relates to organic electronic devices comprising such compounds.

BACKGROUND AND DESCRIPTION OF THE PRIOR ART

In recent years, major efforts have been made to develop organic semiconducting (OSC) materials in order to be able to produce more versatile, lower cost electronic devices. Such materials find application in a wide range of devices or apparatus, such as for example organic field effect transistors (OFETs), organic light emitting diodes (OLEDs), photodetectors, organic photovoltaic (OPV) cells, sensors, memory elements and logic circuits to name a few only. The organic semiconducting materials are generally present in the electronic device in the form of a thin layer of, for example, between 50 and 300 nm thickness.

Polycyclic aromatic compounds, either as "small molecules", such as for example pentacene, or in form of polymers, such as for example poly(hexylthiophene), are widely used in organic electronics because of their good semiconducting properties, However, these materials have a number of disadvantages, which hinder large-scale commercial production. In general these polycyclic aromatic compounds are characterized by low solubility and in consequence can often be processed by vapor deposition methods only. Furthermore they are also difficult to synthesize and in some cases, such as for example pentacene, extremely sensitive to oxidation. On top of this, their charge-carrier mobility and on/off ratio still leave room for improvement.

A promising class of conjugated polymers is based on the indenofluorene unit and was first reported in S. Setayesh et al., Macromolecules 2000, 33, 2016-2020 (DOI: 10.1021/ma9914366) as a candidate material for blue light emission in electroluminescent applications. Indenofluorene copolymers have also been disclosed in WO 2007/131582 for application as organic semiconducting material in transistor devices.

Polymers comprising indacenodithiophene units have been disclosed for example in WO 2012/174561; in WO 2012/088698; in EP 2 075 274 A1; in W. Wen et al., Chem. Commun., 2013, 49, 7192 (DOI: 10.1039/c3cc43229g); in C. Y. Yu et al., Chem. Mater. 2009, 21, 3262-3269 (DOI: 10.1021/cm9007798); in C. P. Chen et al., J. Am. Chem. Soc. 2008, 130, 12828-12833; in Y. Sun et al., J. Mater. Chem., 2011, 21, 13247 (DOI: 10.1039/cljm11564b); in J. H. Tsai et al., Journal of Polymer Science: Part A: Polymer Chemistry, Vol. 48, 2351-2360 (2010) (DOI: 10.1002/pola.24002); in Y. Zhang et al., Macromolecules 2011, 44, 4752-4758 (DOI: 10.1021/ma2008699); in S. H. Chan et al., Macromolecules 2008, 41, 5519-5526 (DOI: 10.1021/ma800494k); in I. McCulloch et al., Nature Materials, vol. 5, April 2006, pages 328-333 (DOI: 10.1038/nmat1612); and in Y. C. Chen et al., J. Sol. Energy Eng. 132(2), 021103 (May 3, 2010) (DOI: 10.1115/1.4001150).

However, the reported charge-carrier mobilities reach at best 0.2 cm$^2$/Vs while most of the reported values are well below 0.1 cm$^2$/Vs.

It is therefore an objective of the present invention to provide new organic semiconducting materials for use in electronic devices. Preferably, such new organic semiconducting materials are characterized by advantageous properties in one or more of good processability, high charge-carrier mobility, high on/off ratio, good oxidative stability and long lifetime in electronic devices. Additionally, it is an objective of the present invention to extend the pool of semiconducting materials available to the expert. Other objectives of the present application are immediately evident to the expert from the following detailed description and examples

SUMMARY OF THE INVENTION

The present inventors have now surprisingly found that the above objectives may be attained either individually or in any combination by the compound of the present application.

The present application therefore provides for a compound comprising at least one constitutional unit M selected from the group consisting of formula (I-a) and formula (I-b)

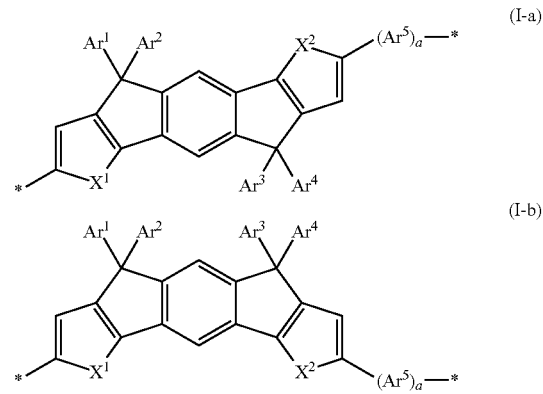

wherein

X$^1$ and X$^2$ are independently of each other S or Se;

Ar$^1$, Ar$^2$, Ar$^3$ and Ar$^4$ are independently of each other heteroaryl having from 5 to 30 aromatic ring atoms, said heteroaryl being unsubstituted or substituted with one or more groups R$^S$;

a is 0 or an integer from 1 to 10;

Ar$^5$ is at each occurrence independently selected from the group consisting of —CR$^S$=CR$^S$—, —C≡C—, arylene having from 6 to 30 aromatic carbon atoms and heteroarylene having from 5 to 30 aromatic ring atoms, wherein said arylene or heteroarylene may be unsubstituted or substituted with one or more groups R$^S$;

R$^S$ is at each occurrence independently selected from the group consisting of any group R$^T$ as defined herein, hydrocarbyl having from 1 to 40 carbon atoms wherein the hydrocarbyl may be further substituted with one or more groups R$^T$ and hydrocarbyl having from 1 to 40 carbon atoms comprising one or more heteroatoms selected from the group consisting of N, O, S, P, Si, Se, As, Te or Ge, with N, O and S being preferred heteroatoms, wherein the hydrocarbyl may be further substituted with one or more groups R$^T$;

R$^T$ is at each occurrence independently selected from the group consisting of F, Br, Cl, —CN, —NC, —NCO, —NCS, —OCN, —SCN, —C(O)NR$^0$R$^{00}$, —C(O)X$^0$, —C(O)R⁰, —NH₂, —NR⁰R⁰⁰, —SH, —SR⁰, —SO₃H, —SO₂R⁰, —OH, —OR⁰, —NO₂, —SF₅ and —SiR⁰R⁰⁰R⁰⁰⁰;

R⁰, R⁰⁰ and R⁰⁰⁰ are at each occurrence independently of each other selected from the group consisting of H, F, hydrocarbyl having from 1 to 40 carbon atoms; and X⁰ is halogen.

The present application also provides for a blend or mixture comprising said compound and one or more compounds selected from the group consisting of binders and compounds or polymers having semiconducting, charge transport, charge blocking, photoconducting or light emitting properties.

Further, the present application provides for a formulation comprising said compound and at least one organic solvent.

In addition, the present application provides for a material or layer comprised in an electronic device, said material or layer comprising the compound of the present application and said material or layer having charge transport, semiconducting, electrically conducting, photoconducting or light emitting properties.

Furthermore, the present application provides for an electronic device comprising the compound of the present application.

BRIEF DESCRIPTION OF THE FIGURE

FIG. 1 shows the transfer characteristics and the charge carrier mobility of the top-gate organic field-effect transistor (OFET) of Example 1 prepared using Polymer 1.

DETAILED DESCRIPTION OF THE INVENTION

For the purposes of the present application an asterisk ("*") denotes a linkage to an adjacent unit or group or, in case of a polymer, to an adjacent repeating unit or any other group, such as for example a terminal group or an endcap group.

In the present application the term "arylene" is used to denote a bivalent group derived from an arene by removal of a hydrogen atom from two ring carbon atoms (International Union of Pure and Applied Chemistry, Compendium of Chemical Technology, Gold Book, Version 2.3.2, 2012-08-19, page 115). In the present application the term "heteroarylene" is used correspondingly to denote bivalent groups derived from a heteroarene by removal of a hydrogen from two ring carbon atoms.

As used herein, the term "conjugated" will be understood to mean a compound (for example a polymer) that contains mainly C atoms with sp²-hybridization (or optionally also sp-hybridization), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound. See also International Union of Pure and Applied Chemistry, Compendium of Chemical Technology, Gold Book, Version 2.3.2, 19. August 2012, pages 322-323.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, chlorobenzene is used as solvent. The molecular weight distribution ("MWD"), which may also be referred to as polydispersity index ("PDI"), of a polymer is defined as the ratio $M_w/M_n$. The degree of polymerization, also referred to as total number of repeat units, m, will be understood to mean the number average degree of polymerization given as $m=M_n/M_U$, wherein $M_n$ is the number average molecular weight of the polymer and $M_U$ is the molecular weight of the single repeat unit; see J. M. G. Cowie, *Polymers: Chemistry & Physics of Modern Materials*, Blackie, Glasgow, 1991.

As used herein, the term "organyl" or "organyl group" is to denote any organic substituent group, regardless of functional type, having one or more free valence at a carbon atom (see also International Union of Pure and Applied Chemistry, Compendium of Chemical Technology, Gold Book, Version 2.3.2, 2012-08-09, page 1040).

As used herein, the term "organoheteryl" or "organoheteryl group" is used to denote any univalent or polyvalent groups comprising carbon, which are thus organic, but which have their free valence at an atom other than carbon (see also International Union of Pure and Applied Chemistry, Compendium of Chemical Technology, Gold Book, Version 2.3.2, 2012-08-09, page 1038).

As used herein, the term "hetero atom" will be understood to mean an atom in an organic compound that is not a H- or C-atom, and preferably will be understood to mean N, O, S, P, Si, Se, As, Te or Ge, unless specified otherwise.

Constitutional Unit M

The present inventors have surprisingly found that the properties of an indacenodithiophene compound can be significantly improved by specifically selecting the substituents on the indacenodithiophene unit.

The compound of the present invention therefore comprises at least one constitutional (or structural) unit M selected from the group consisting of formula (I-a) and formula (I-b)

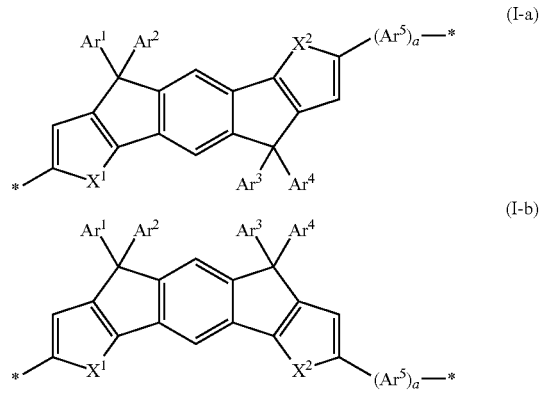

wherein $X^1$, $X^2$, $Ar^1$, $Ar^2$, $Ar^3$, $Ar^4$, $Ar^5$ and a are as defined in the following.

$X^1$ and $X^2$ are independently of each other S or Se. Preferably, $X^1$ and $X^2$ are both S.

Preferably, said constitutional unit M is of formula (I-a). More preferably, said constitutional unit M is of formula (I-a) with $X^1$ and $X^2$ both being S.

Ar¹, Ar², Ar³ and Ar⁴ are independently of each other heteroaryl having from 5 to 30, preferably from 5 to 18, aromatic ring atoms, said heteroaryl being unsubstituted or substituted with one or more groups $R^S$ as defined herein.

Preferred examples of Ar¹, Ar², Ar³ and Ar⁴ may be selected from the group consisting of the following formulae (H-1) to (H-34)

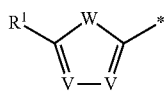 (H-1)

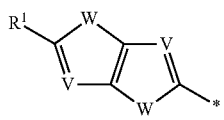 (H-2)

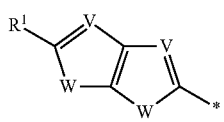 (H-3)

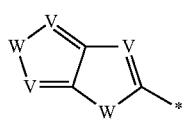 (H-4)

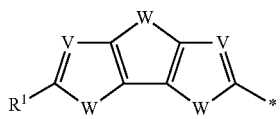 (H-5)

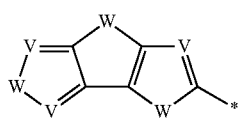 (H-6)

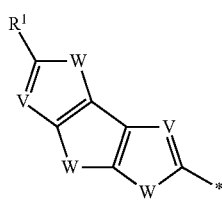 (H-7)

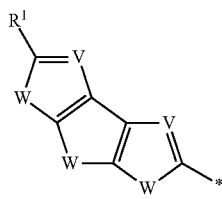 (H-8)

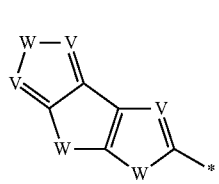 (H-9)

-continued

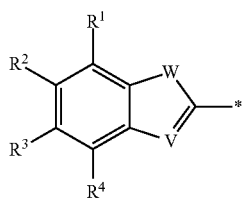 (H-10)

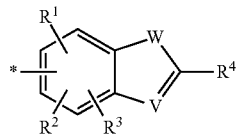 (H-11)

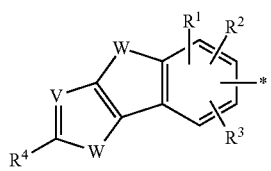 (H-12)

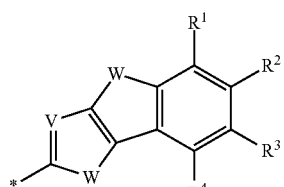 (H-13)

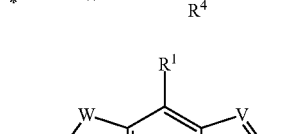 (H-14)

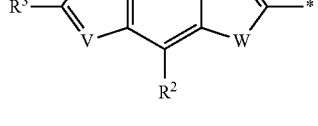 (H-15)

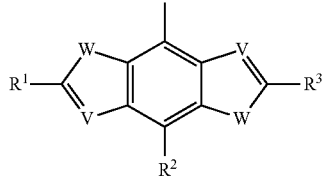 (H-16)

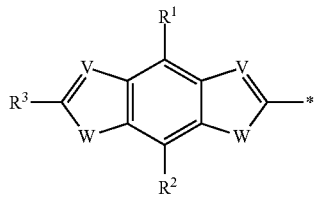 (H-17)

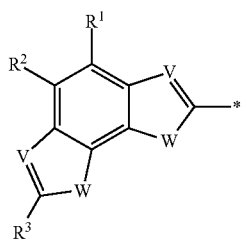 (H-18)
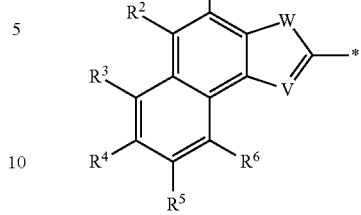
(H-24)
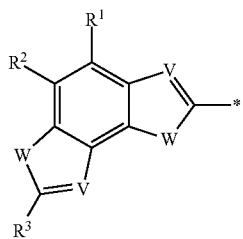 (H-19)
(H-25)
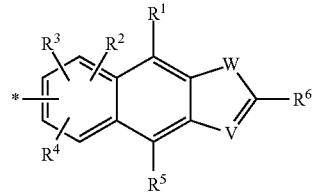
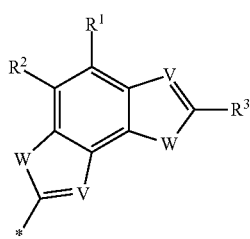 (H-20)
(H-26)
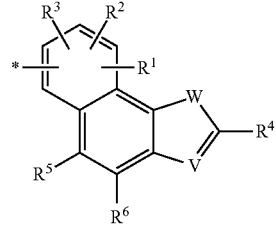
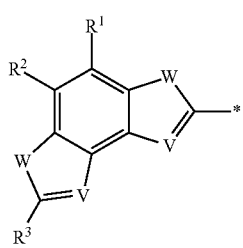 (H-21)
(H-27)
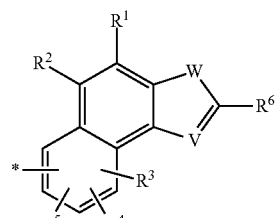
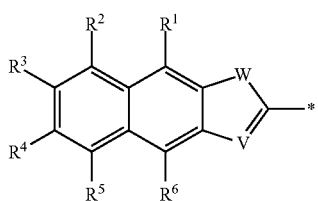 (H-22)
(H-28)
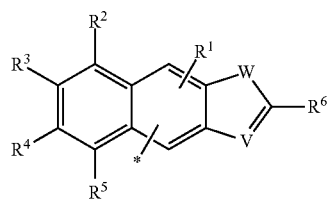
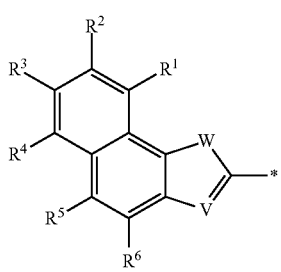 (H-23)
(H-29)
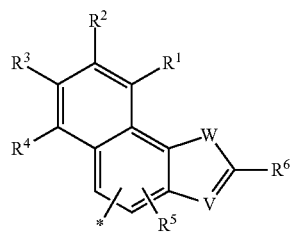
(H-30)
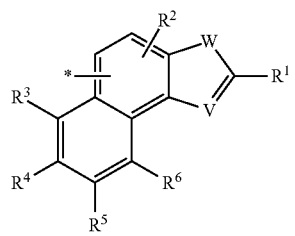

-continued

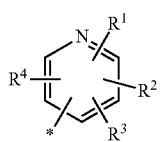
(H-31)

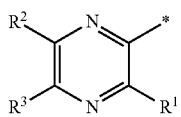
(H-32)

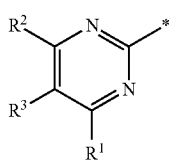
(H-33)

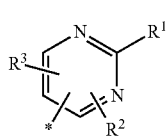
(H-34)

wherein V, W, $R^1$, $R^2$, $R^3$, $R^4$, $R^5$ and $R^6$ are as defined herein.

Of formulae (H-1) to (H-34), formulae (H-1), (H-2) and (H-31) are preferred, with (H-1) and (H-2) being more preferred.

V is at each occurrence independently $CR^7$ or N.

W is at each occurrence independently selected from the group consisting of O, S and Se. Preferably W is at each occurrence S.

$R^1$, $R^2$, $R^3$, $R^4$, $R^5$, $R^6$ and any $R^7$ present are independently of each other selected from the group consisting of H and $R^S$.

$R^S$ is at each occurrence independently selected from the group consisting of any group $R^T$ as defined herein, hydrocarbyl having from 1 to 40 carbon atoms wherein the hydrocarbyl may be further substituted with one or more groups $R^T$ and hydrocarbyl having from 1 to 40 carbon atoms comprising one or more heteroatoms selected from the group consisting of N, O, S, P, Si, Se, As, Te or Ge, with N, O and S being preferred heteroatoms, wherein the hydrocarbyl may be further substituted with one or more groups $R^T$.

Preferred examples of hydrocarbyl suitable as $R^S$ may at each occurrence be independently selected from phenyl, phenyl substituted with one or more groups $R^T$, alkyl and alkyl substituted with one or more groups $R^T$, wherein the alkyl has at least 1, preferably at least 5, more preferably at least 10 and most preferably at least 15 carbon atoms and/or has at most 40, more preferably at most 30, even more preferably at most 25 and most preferably at most 20 carbon atoms. It is noted that for example alkyl suitable as $R^S$ also includes fluorinated alkyl, i.e. alkyl wherein one or more hydrogen is replaced by fluorine, and perfluorinated alkyl, i.e. alkyl wherein all of the hydrogen are replaced by fluorine.

$R^T$ is at each occurrence independently selected from the group consisting of F, Br, Cl, —CN, —NC, —NCO, —NCS, —OCN, —SCN, —C(O)$NR^oR^{oo}$, —C(O)$X^o$, —C(O)$R^o$, —$NH_2$, —$NR^oR^{oo}$, —SH, —$SR^o$, —$SO_3H$, —$SO_2R^o$, —OH, —$OR^o$, —$NO_2$, —$SF_5$ and —$SiR^oR^{oo}R^{ooo}$. Preferred $R^T$ are selected from the group consisting of F, Br, Cl, —CN, —NC, —NCO, —NCS, —OCN, —SCN, —C(O)$NR^oR^{oo}$, —C(O)$X^o$, —C(O)$R^o$, —$NH_2$, $NR^oR^{oo}$, —SH, —$SR^o$, —OH, —$OR^o$ and —$SiR^oR^{oo}R^{ooo}$. Most preferred $R^T$ is F.

$R^o$, $R^{oo}$ and $R^{ooo}$ are at each occurrence independently of each other selected from the group consisting of H, F, hydrocarbyl having from 1 to 40 carbon atoms. Said hydrocarbyl preferably have at least 5, more preferably at least 10 and most preferably at least 15 carbon atoms. Said hydrocarbyl preferably have at most 30, even more preferably at most 25 and most preferably at most 20 carbon atoms. Preferably, $R^o$, $R^{oo}$ and $R^{ooo}$ are at each occurrence independently of each other selected from the group consisting of H, F, alkyl, fluorinated alkyl, alkenyl, alkynyl, phenyl and fluorinated phenyl. More preferably, $R^o$, $R^{oo}$ and $R^{ooo}$ are at each occurrence independently of each other selected from the group consisting of H, F, alkyl, fluorinated, preferably perfluorinated, alkyl, phenyl and fluorinated, preferably perfluorinated, phenyl.

It is noted that for example alkyl suitable as $R^o$, $R^{oo}$ and $R^{ooo}$ also includes perfluorinated alkyl, i.e. alkyl wherein all of the hydrogen are replaced by fluorine. Examples of alkyls may be selected from the group consisting of methyl, ethyl, n-propyl, iso-propyl, n-butyl, iso-butyl, tert-butyl (or "t-butyl"), pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl (—$C_{20}H_{41}$).

$X^o$ is halogen. Preferably $X^o$ is selected from the group consisting of F, Cl and Br.

A hydrocarbyl group comprising a chain of 3 or more carbon atoms and heteroatoms combined may be straight chain, branched and/or cyclic, including spiro and/or fused rings.

Hydrocarbyl suitable as $R^S$, $R^o$, $R^{oo}$ and/or $R^{ooo}$ may be saturated or unsaturated. Examples of saturated hydrocarbyl include alkyl. Examples of unsaturated hydrocarbyl may be selected from the group consisting of alkenyl (including acyclic and cyclic alkenyl), alkynyl, allyl, alkyldienyl, polyenyl, aryl and heteroaryl.

Preferred hydrocarbyl suitable as $R^S$, $R^o$, $R^{oo}$ and/or $R^{ooo}$ include hydrocarbyl comprising one or more heteroatoms and may for example be selected from the group consisting of alkoxy, alkylcarbonyl, alkoxycarbonyl, alkylcarbonyloxy and alkoxycarbonyloxy, alkylaryloxy, arylcarbonyl, aryloxycarbonyl, arylcarbonyloxy and aryloxycarbonyloxy.

Preferred examples of aryl and heteroaryl comprise mono-, bi- or tricyclic aromatic or heteroaromatic groups that may also comprise condensed rings.

Especially preferred aryl and heteroaryl groups may be selected from the group consisting of phenyl, phenyl wherein one or more CH groups are replaced by N, naphthalene, fluorene, thiophene, pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, dithienothiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole and benzothiadiazole.

Preferred examples of an alkoxy group, i.e. a corresponding alkyl group wherein the terminal $CH_2$ group is replaced by —O—, can be straight-chain or branched, preferably straight-chain (or linear). Suitable examples of such alkoxy group may be selected from the group consisting of methoxy, ethoxy, propoxy, butoxy, pentoxy, hexoxy, heptoxy, octoxy, nonoxy, decoxy, undecoxy, dodecoxy, tridecoxy, tetradecoxy, pentadecoxy, hexadecoxy, heptadecoxy and octadecoxy.

Preferred examples of alkenyl, i.e. a corresponding alkyl wherein two adjacent $CH_2$ groups are replaced by —CH═CH— can be straight-chain or branched. It is preferably straight-chain. Said alkenyl preferably has 2 to 10 carbon atoms. Preferred examples of alkenyl may be selected from the group consisting of vinyl, prop-1-enyl, or prop-2-enyl, but-1-enyl, but-2-enyl or but-3-enyl, pent-1-enyl, pent-2-enyl, pent-3-enyl or pent-4-enyl, hex-1-enyl, hex-2-enyl, hex-3-enyl, hex-4-enyl or hex-5-enyl, hept-1-enyl, hept-2-enyl, hept-3-enyl, hept-4-enyl, hept-5-enyl or hept-6-enyl, oct-1-enyl, oct-2-enyl, oct-3-enyl, oct-4-enyl, oct-5-enyl, oct-6-enyl or oct-7-enyl, non-1-enyl, non-2-enyl, non-3-enyl, non-4-enyl, non-5-enyl, non-6-enyl, non-7-enyl, non-8-enyl, dec-1-enyl, dec-2-enyl, dec-3-enyl, dec-4-enyl, dec-5-enyl, dec-6-enyl, dec-7-enyl, dec-8-enyl and dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Alkenyl groups having up to 5 C atoms are generally preferred.

Preferred examples of oxaalkyl, i.e. a corresponding alkyl wherein one non-terminal $CH_2$ group is replaced by —O—, can be straight-chain or branched, preferably straight chain. Specific examples of oxaalkyl may be selected from the group consisting of 2-oxapropyl (═methoxymethyl), 2-(═ethoxymethyl) or 3-oxabutyl (═2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl and 2-, 3-, 4-, 5-, 6-, 7-, 8- or 9-oxadecyl.

Preferred examples of carbonyloxy and oxycarbonyl, i.e. a corresponding alkyl wherein one $CH_2$ group is replaced by —O— and one of the thereto adjacent $CH_2$ groups is replaced by —C(O)—. may be selected from the group consisting of acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxy-carbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, and 4-(methoxycarbonyl)-butyl.

Preferred examples of thioalkyl, i.e where one $CH_2$ group is replaced by —S—, may be straight-chain or branched, preferably straight-chain. Suitable examples may be selected from the group consisting of thiomethyl (—$SCH_3$), 1-thioethyl (—$SCH_2CH_3$), 1-thiopropyl (—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) and 1-(thiododecyl).

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (═1-methylpropyl), 2-methylbutyl, 2-methylpentyl, 3-methylpentyl, 2-ethylhexyl, 2-propylpentyl, 2-butyloctyl, 2-hexyldecyl, 2-octyldodecyl, 7-decylnonadecyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-butyloctyl, 2-hexyldecyl, 2-octyldodecyl, 7-decylnonadecyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (═methylpropyl), isopentyl (═3-methylbutyl), tert. butyl, isopropoxy, 2-methyl-propoxy and 3-methylbutoxy.

In a preferred embodiment, the organyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

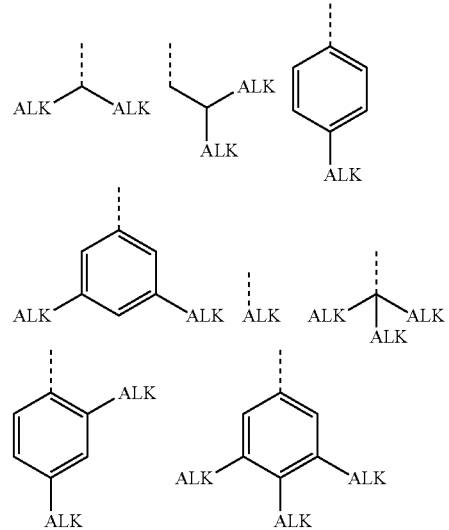

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, —CO—, —C(=O)— and —C(O)— will be understood to mean a carbonyl group, i.e. a group of the following structure

It is noted that if two or more of $Ar^1$, $Ar^2$, $Ar^3$ and $Ar^4$ are any one of formulae (H-1) to (H-34) then these may also differ from each other in terms of the respective groups $R^1$ to $R^6$ and—if present—$R^7$.

a is 0 or an integer of from 1 to 10 (i.e. 1, 2, 3, 4, 5, 6, 7, 8, 9 or 10). Preferably a is an integer of from 1 to 10. More preferably a is an integer of from 1 to 6. Most preferably a is an integer of from 1 to 3.

$Ar^5$ is at each occurrence independently selected from the group consisting of —$CR^S$=$CR^S$—, —C≡C—, arylene having from 6 to 30 aromatic carbon atoms and heteroarylene having from 5 to 30 aromatic ring atoms, wherein said arylene or heteroarylene may be unsubstituted or substituted with one or more groups $R^S$. Preferred heteroarylenes suitable as $Ar^5$ comprise one or more heteroatoms selected from the group consisting of O, S, Se, N and N—$R^0$, with O, S, N and N—$R^0$ being preferred.

Preferably $Ar^5$ may be selected from the group consisting of arylene or heteroarylene having electron donor properties and arylene or heteroarylene having electron acceptor properties, said arylenes or heteroarylenes being unsubstituted or substituted with one or more groups $R^S$ as defined herein.

Preferred examples of $Ar^5$ may be selected from the group consisting of formulae (A1) to (A96) and (D1) to (D140).

Suitable examples of aryl and heteroaryl with electron donor properties may be selected from the group consisting of the following formulae (D1) to (D140)

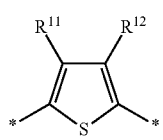
(D1)

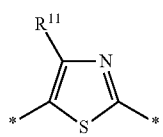
(D2)

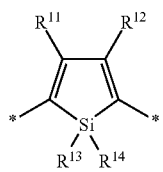
(D3)

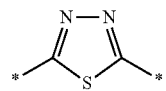
(D4)

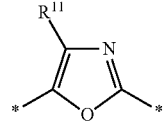
(D5)

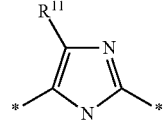
(D6)

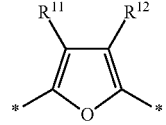
(D7)

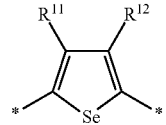
(D8)

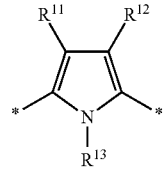
(D9)

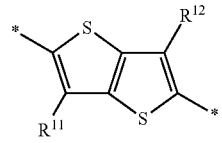
(D10)

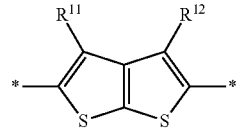
(D11)

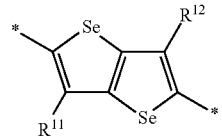
(D12)

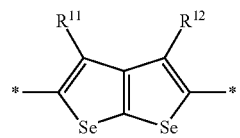
(D13)

(D14)

-continued
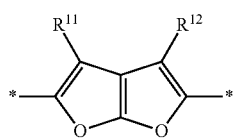 (D15)
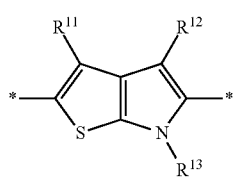 (D16)
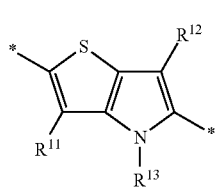 (D17)
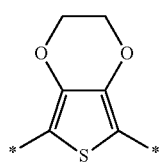 (D18)
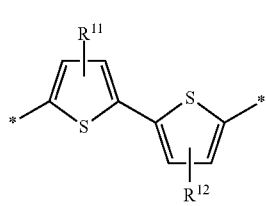 (D19)
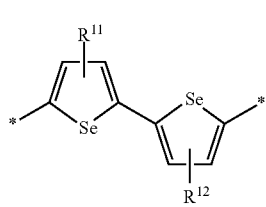 (D20)
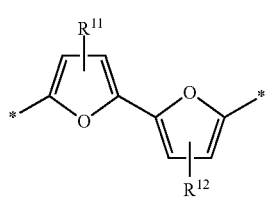 (D21)
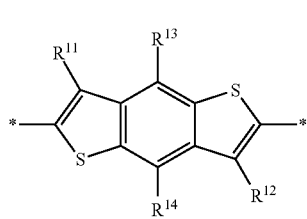 (D22)
-continued
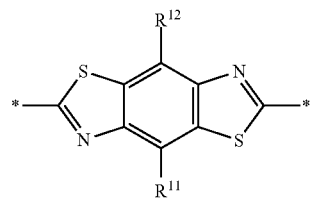 (D23)
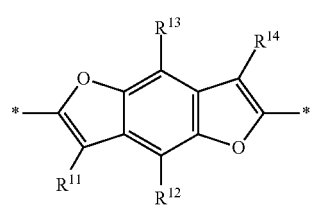 (D24)
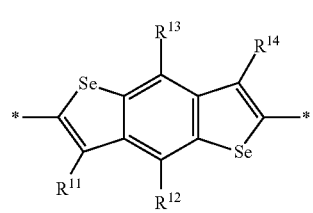 (D25)
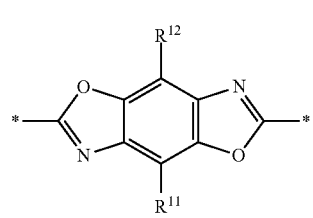 (D26)
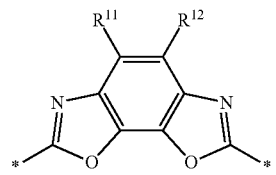 (D27)
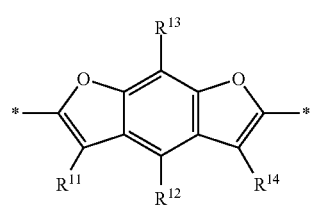 (D28)
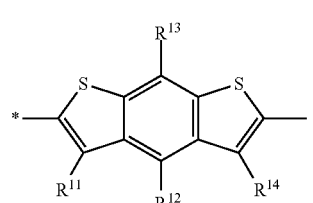 (D29)
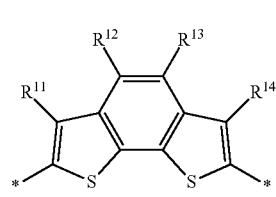 (D30)

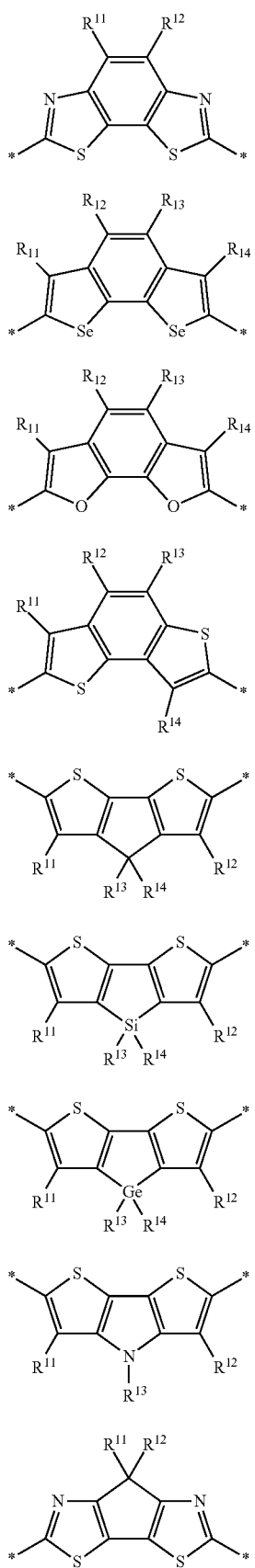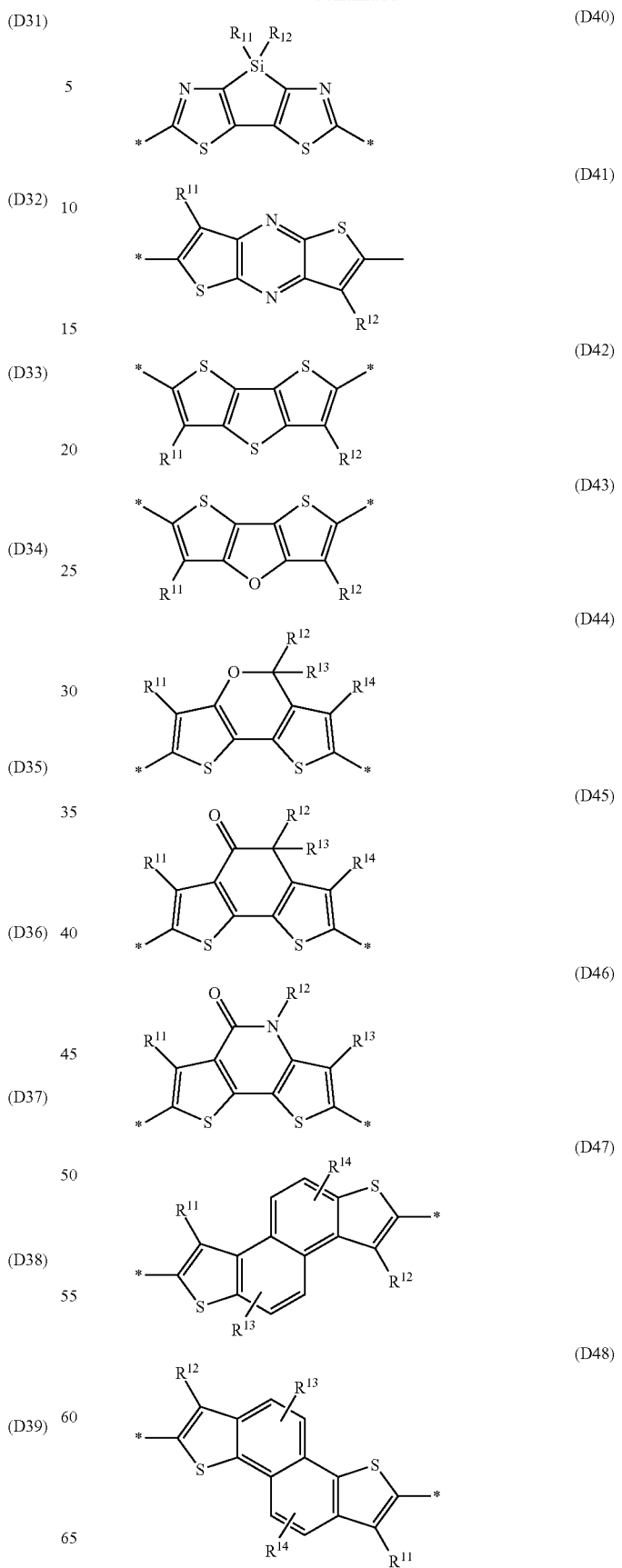

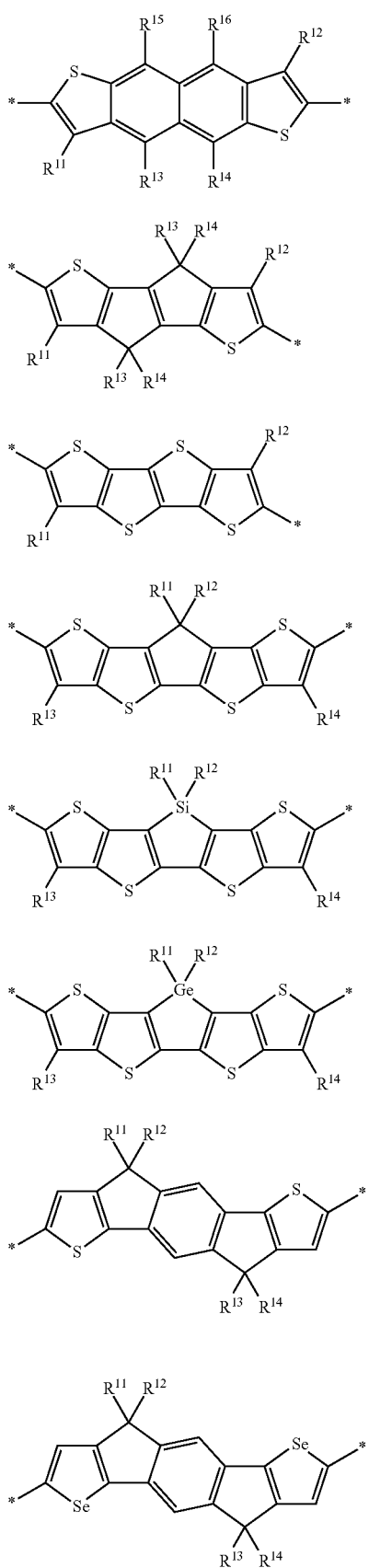
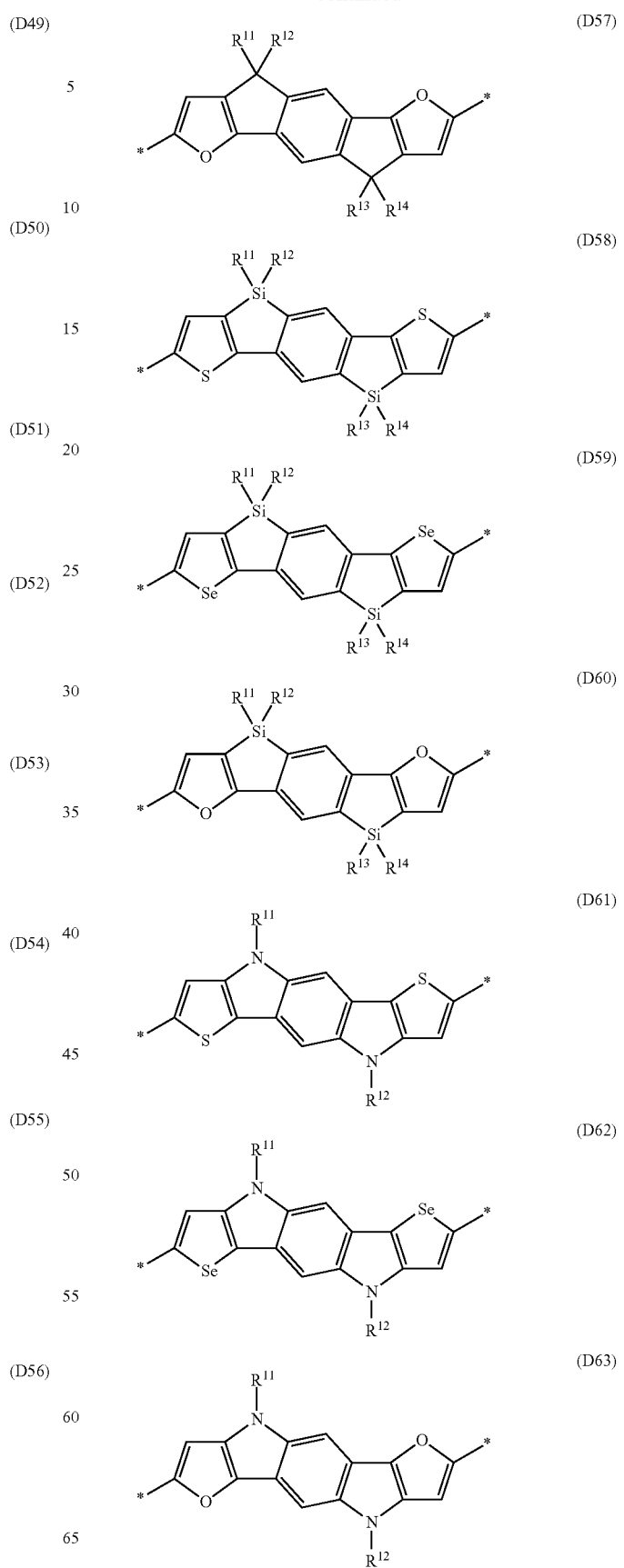

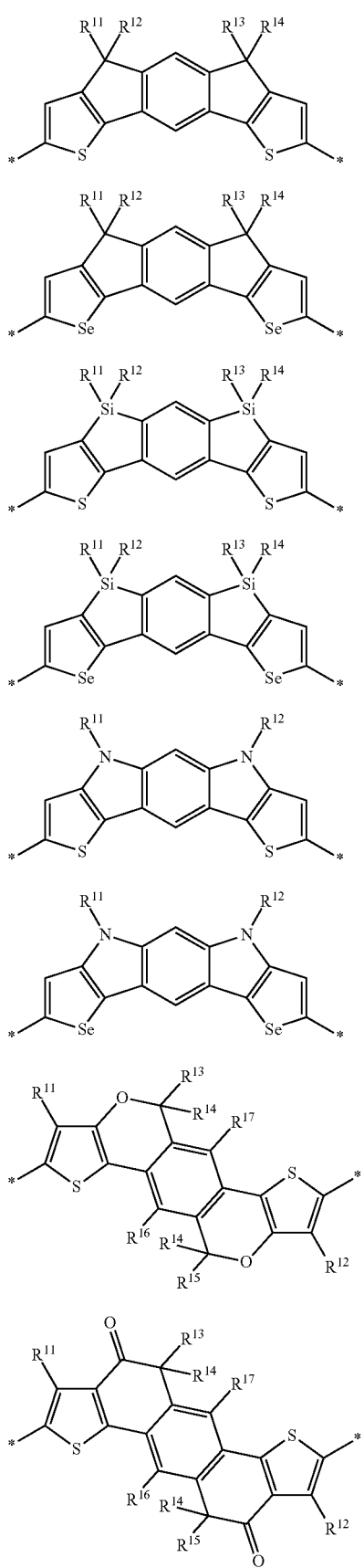
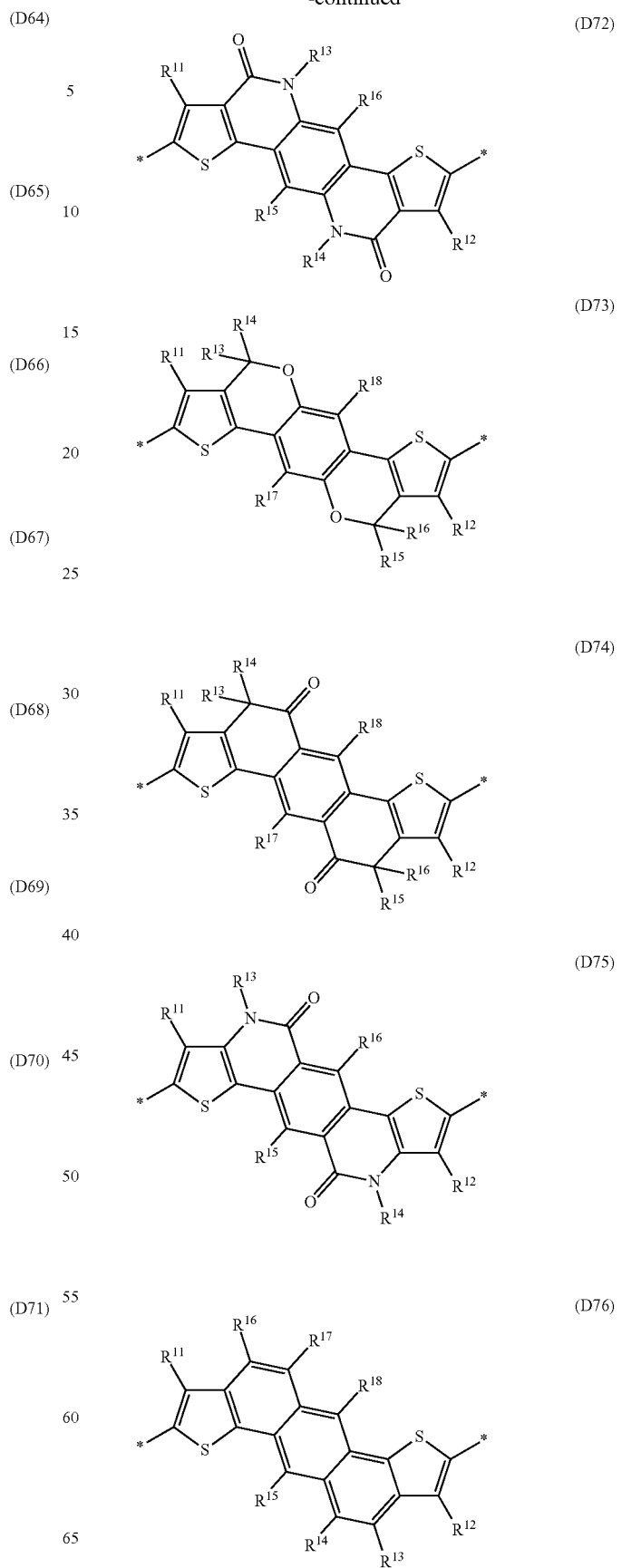

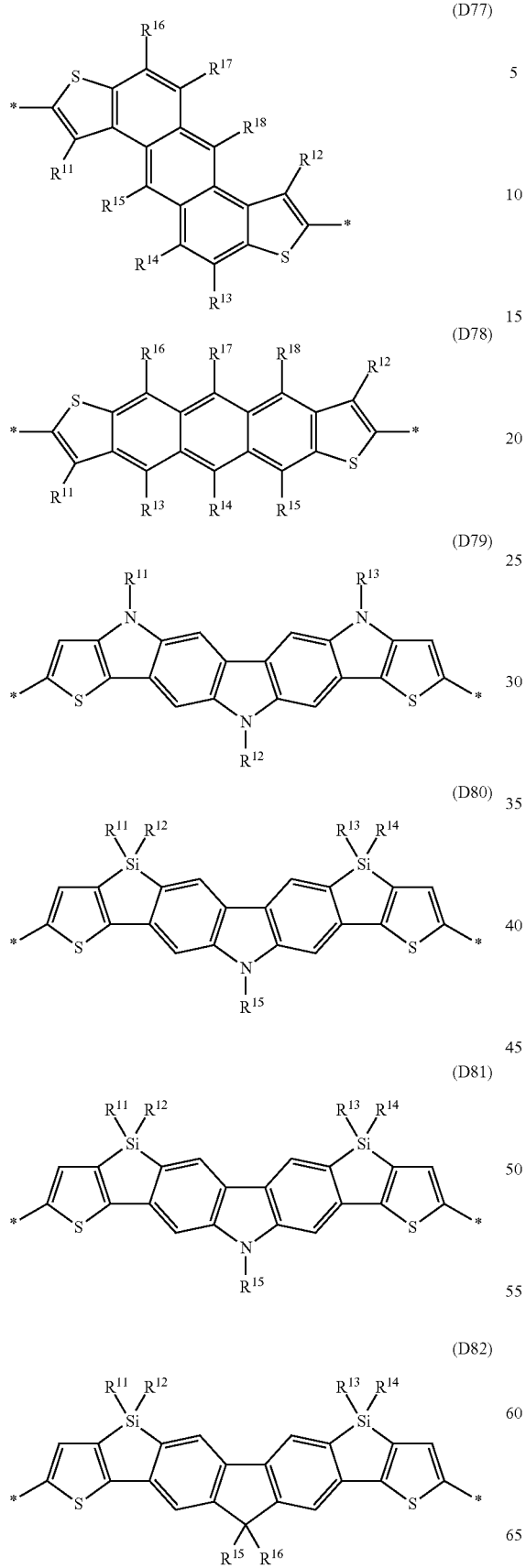
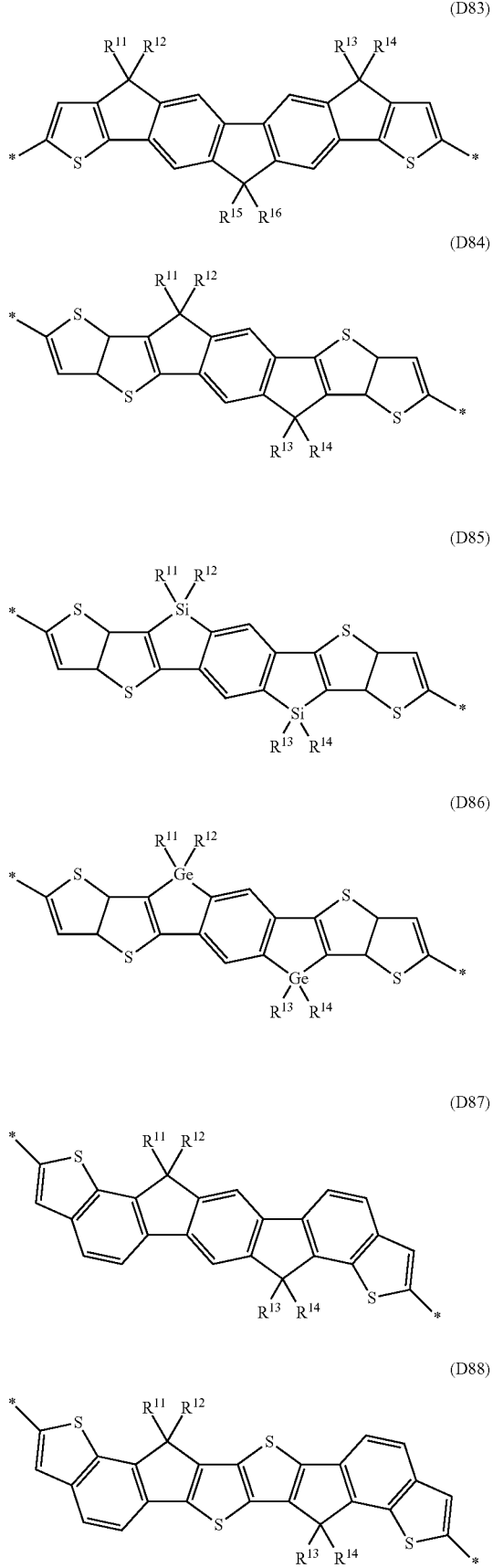

-continued
(D89)
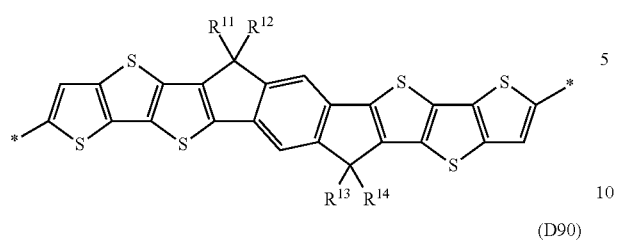
(D90)
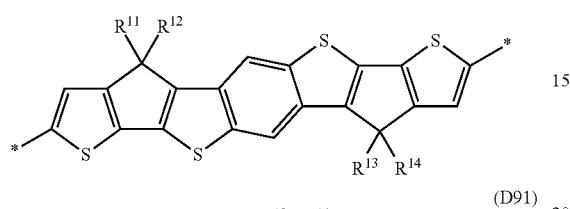
(D91)
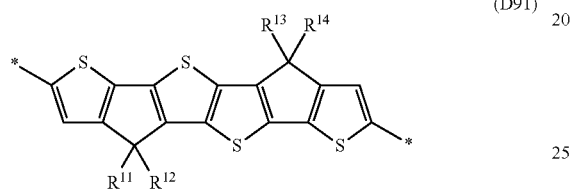
(D92)
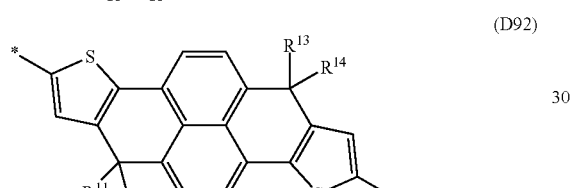
(D93)
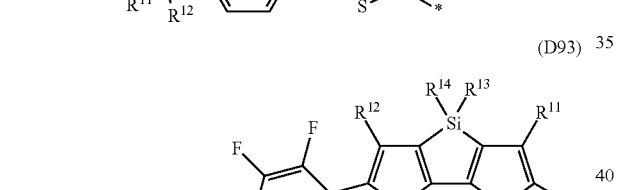
(D94)
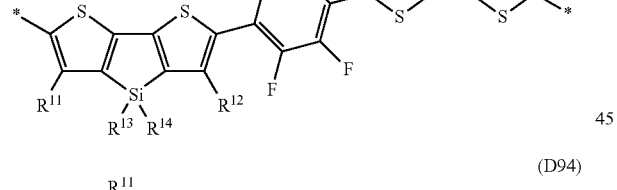
(D95)
(D96)
-continued
(D97)
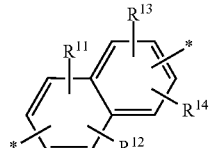
(D98)
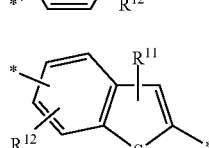
(D99)
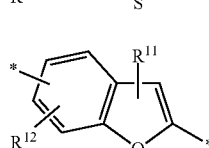
(D100)
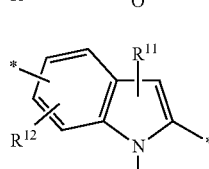
(D101)
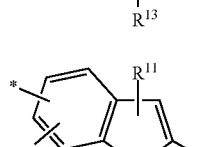
(D102)
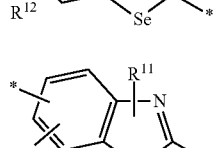
(D103)
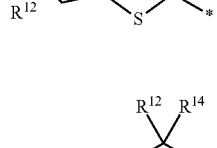
(D104)
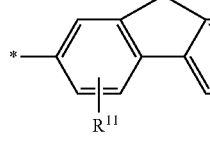
(D105)
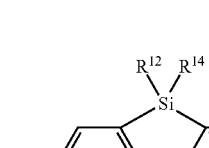

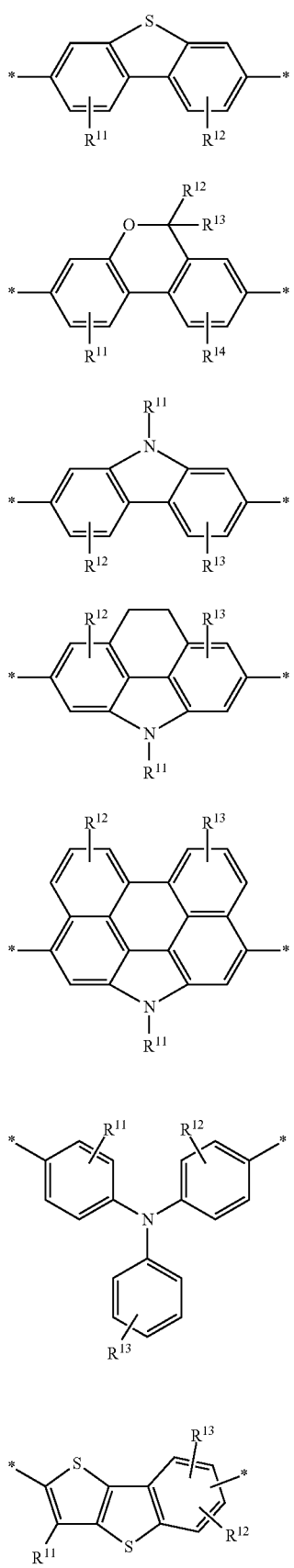
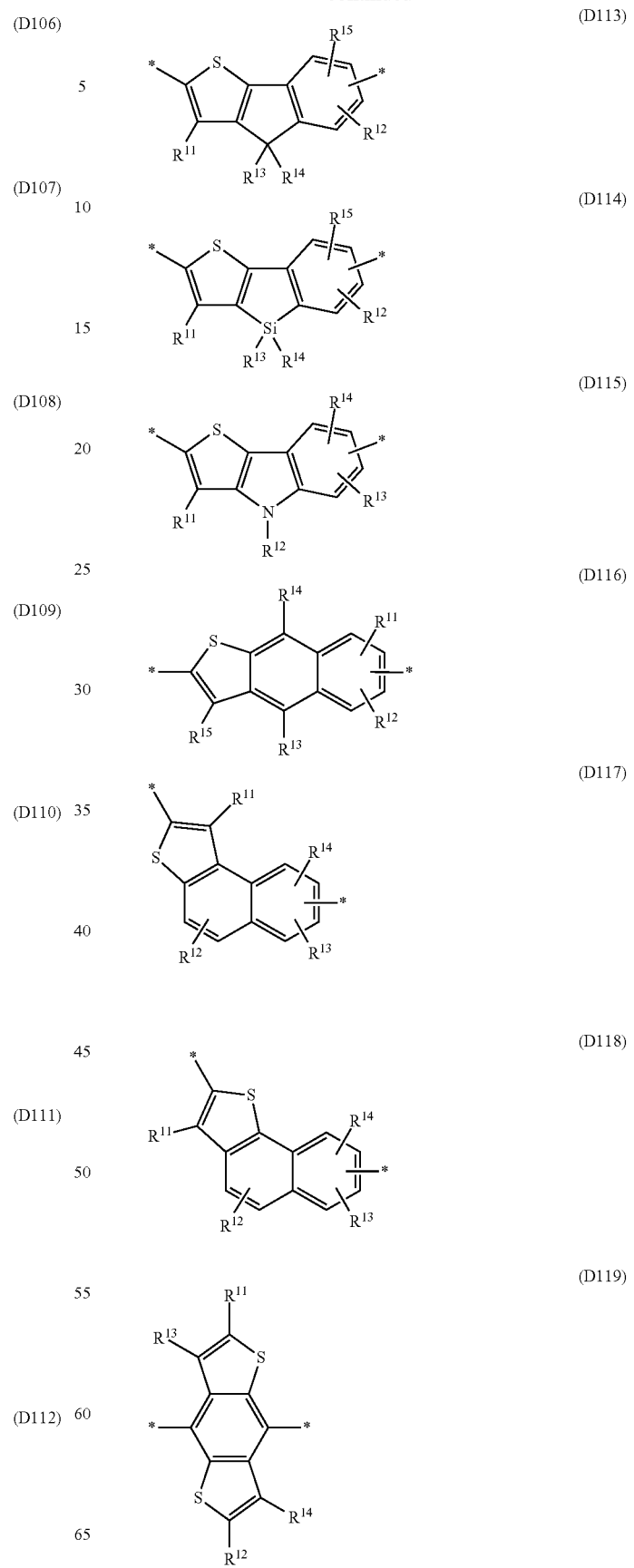

(D120) 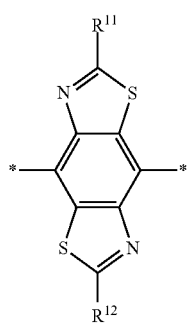
(D121) 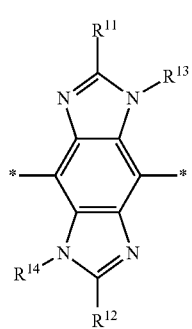
(D122) 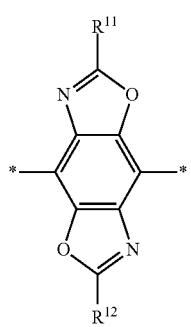
(D123) 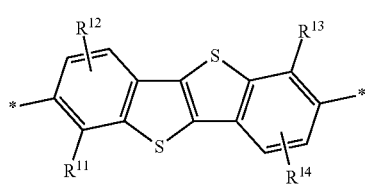
(D124) 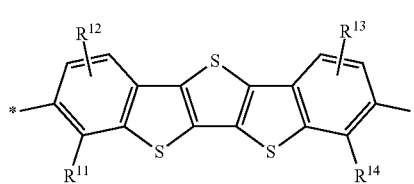
(D125) 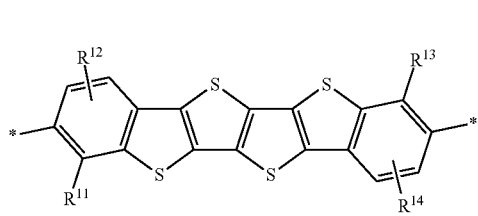
(D126) 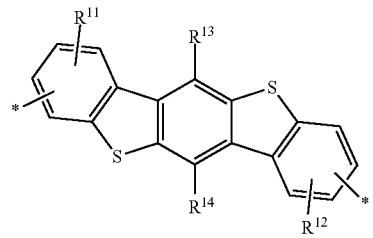
(D127) 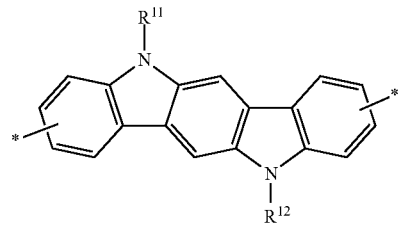
(D128) 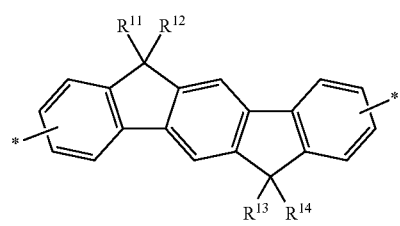
(D129) 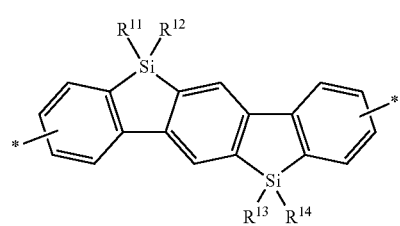
(D130) 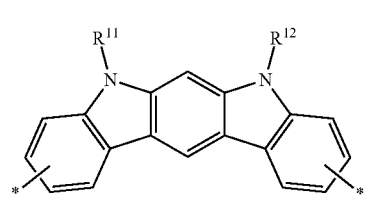
(D131) 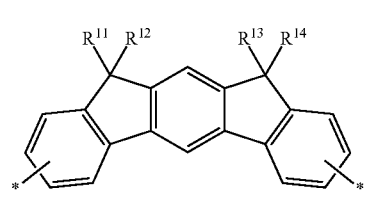
(D132)

-continued
(D133)
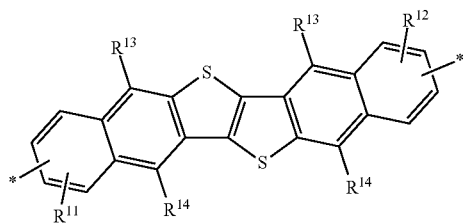
(D134)
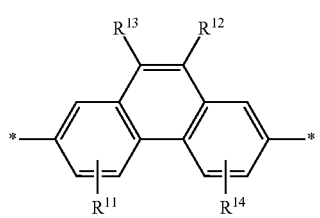
(D135)
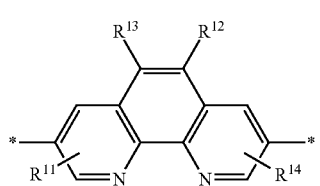
(D136)
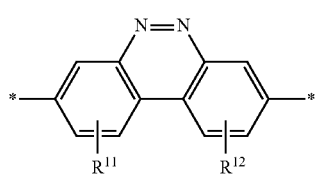
(D137)
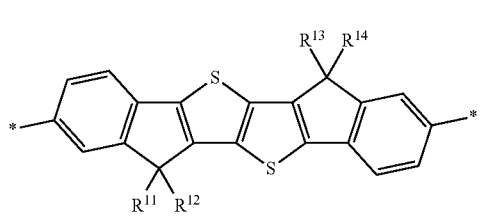
(D138)
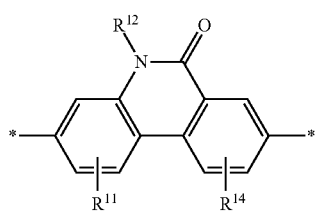
(D139)
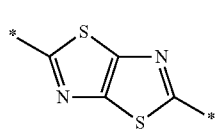
(D140)
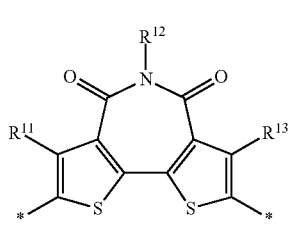
wherein $R^{11}$, $R^{12}$, $R^{13}$, $R^{14}$, $R^{15}$, $R^{16}$, $R^{17}$ and $R^{18}$ are independently of each other selected from the group consisting of H and $R^S$ as defined earlier.
Suitable examples of aryl and heteroaryl with electron acceptor properties may be selected from the group consisting of the following formula (A1) to (A96)
(A1)
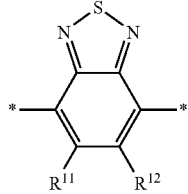
(A2)
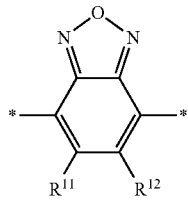
(A3)
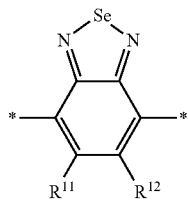
(A4)
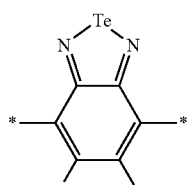
(A5)
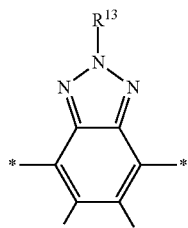
(A6)
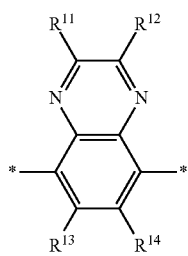

-continued
(A7) 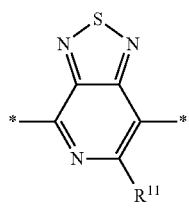
(A8) 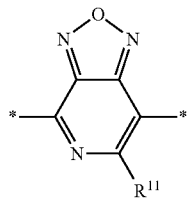
(A9) 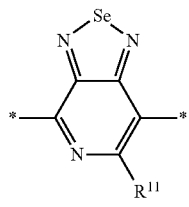
(A10) 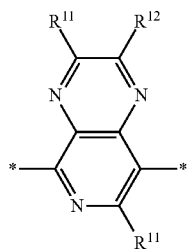
(A11) 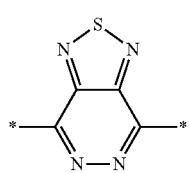
(A12) 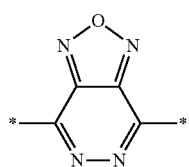
(A13) 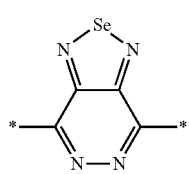
(A14) 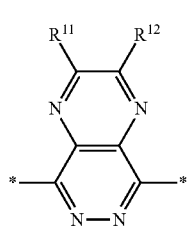
-continued
(A15) 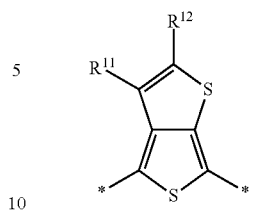
(A16) 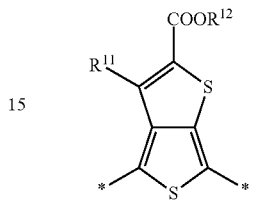
(A17) 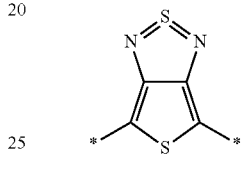
(A18) 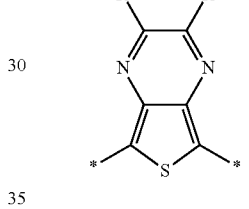
(A19) 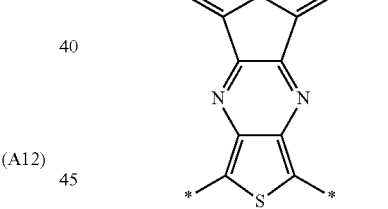
(A20) 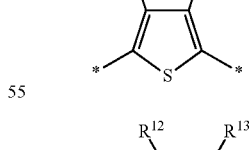
(A21) 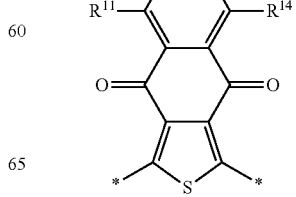

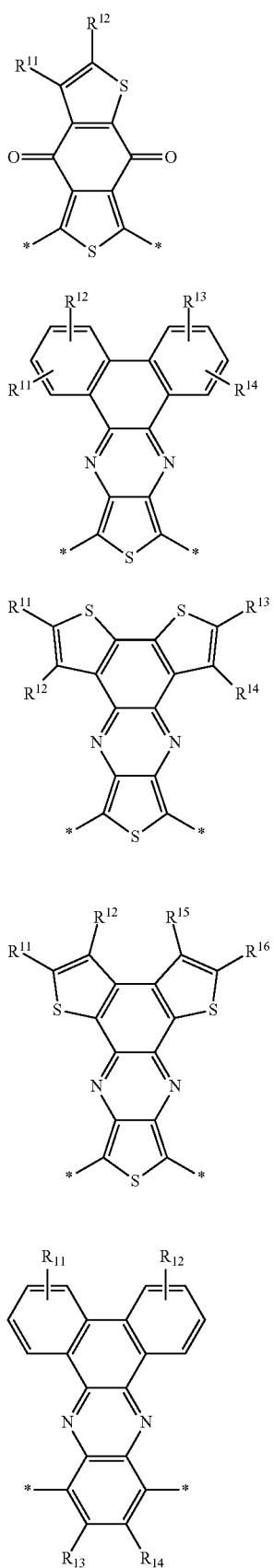
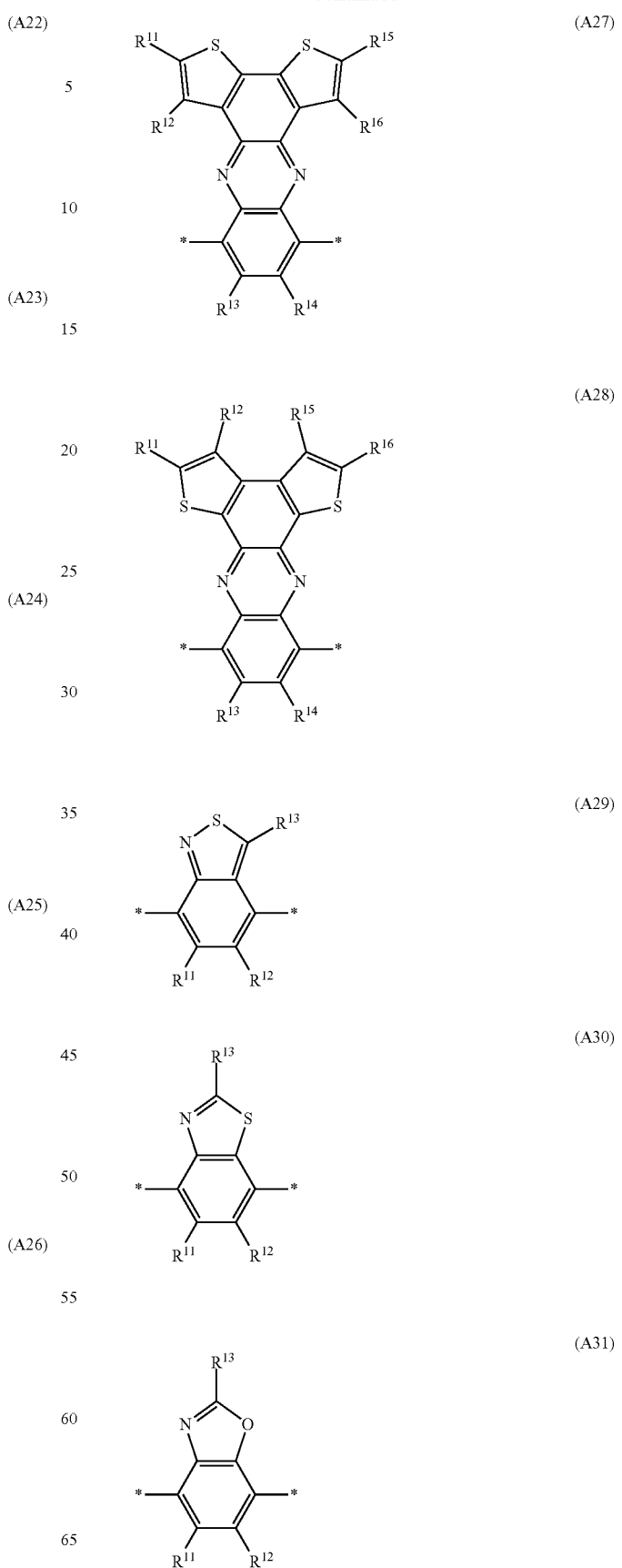

(A32) 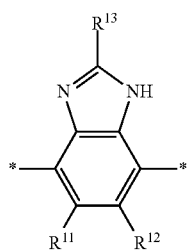
(A33) 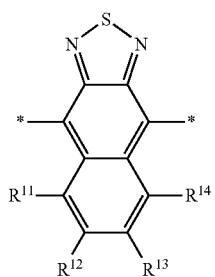
(A34) 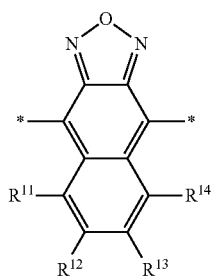
(A35) 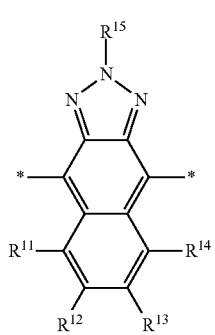
(A36) 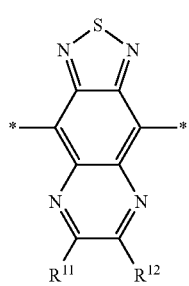
(A37) 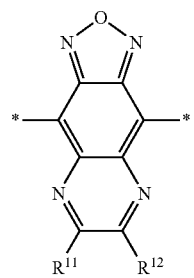
(A38) 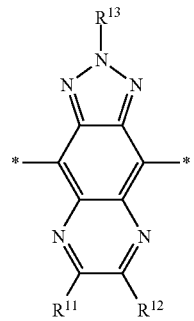
(A39) 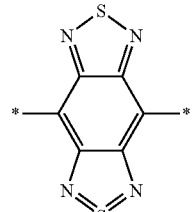
(A40) 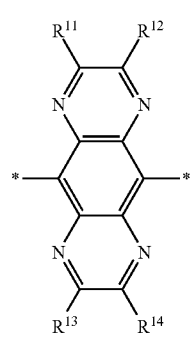
(A41) 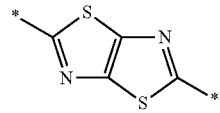
(A42) 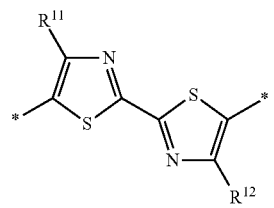
(A43) 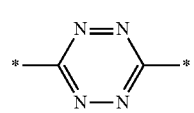

(A44) 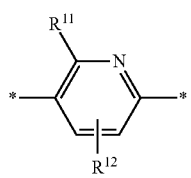
(A45) 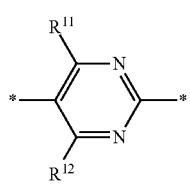
(A46) 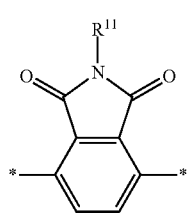
(A47) 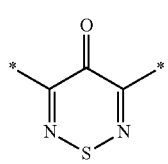
(A48) 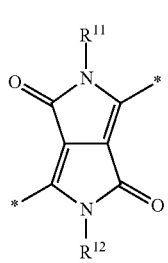
(A49) 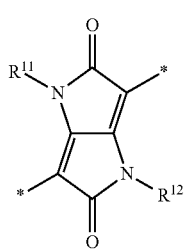
(A50) 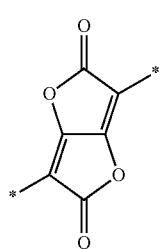
(A51) 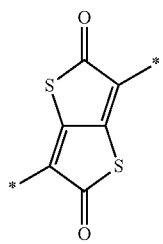
(A52) 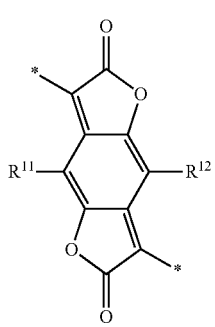
(A53) 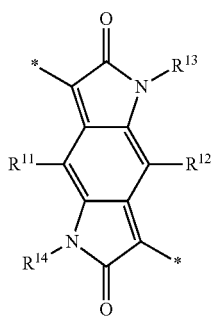
(A54) 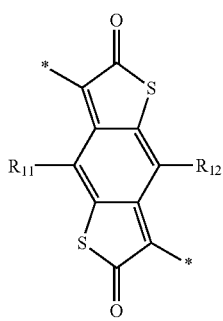
(A55) 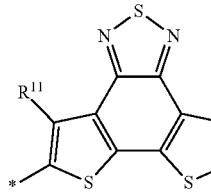

(A56) 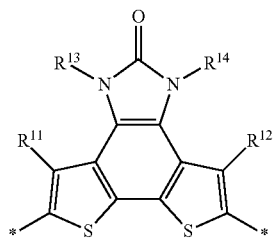
(A57) 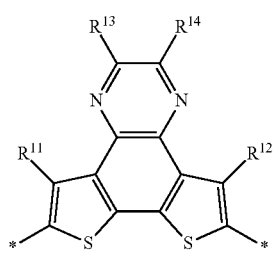
(A58) 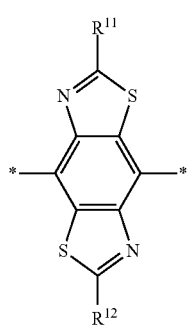
(A59) 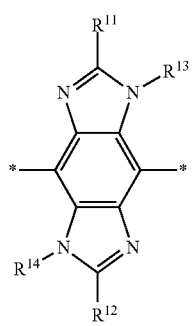
(A60) 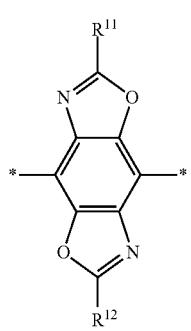
(A61) 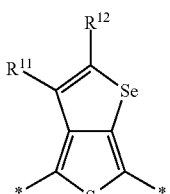
(A62) 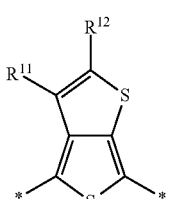
(A63) 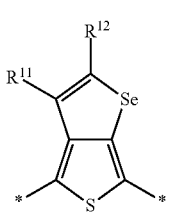
(A64) 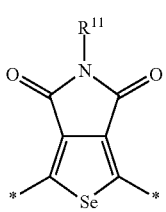
(A65) 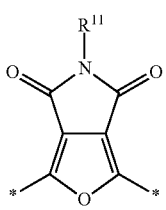
(A66) 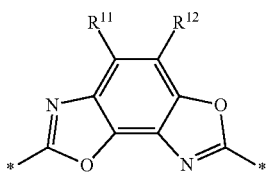
(A67) 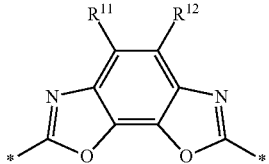
(A68) 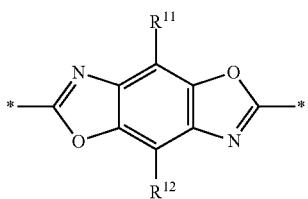

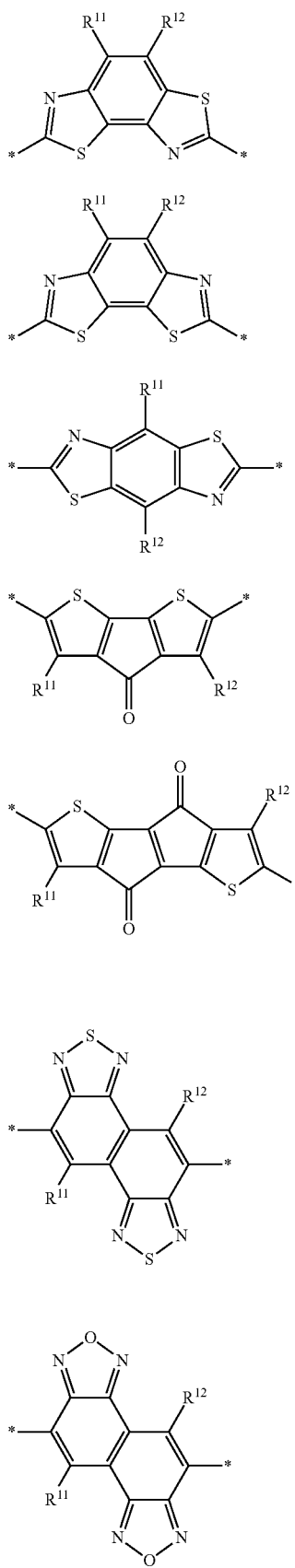
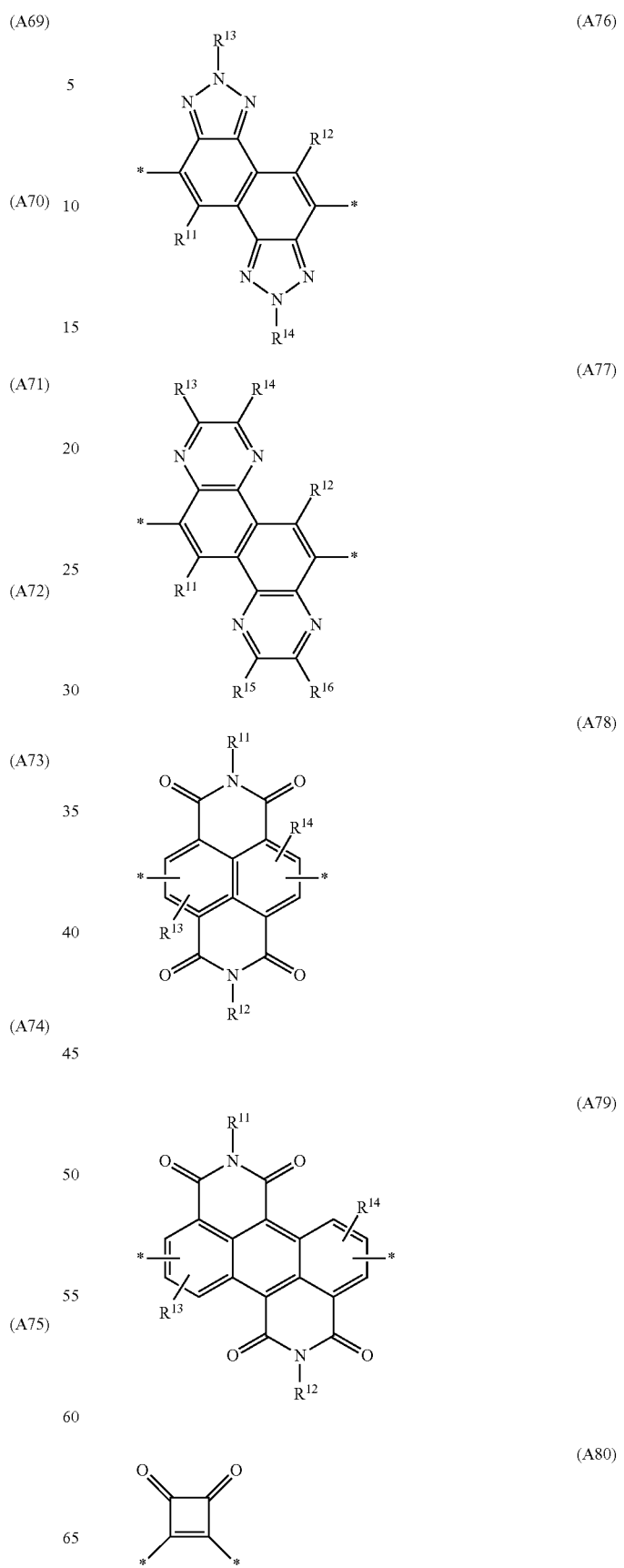

(A81) 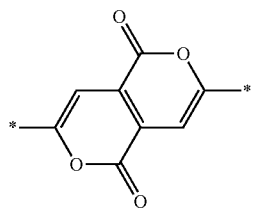
(A82) 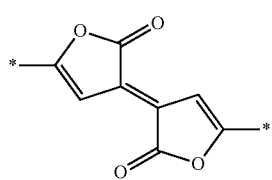
(A83) 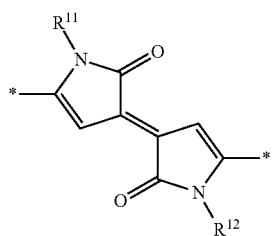
(A84) 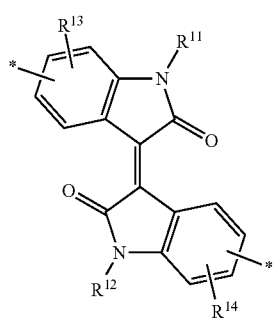
(A85) 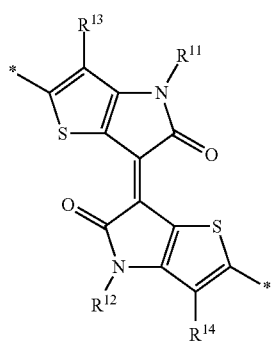
(A86) 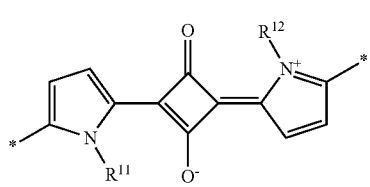
(A87) 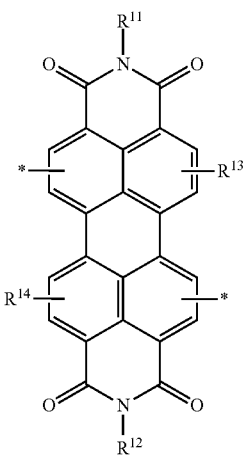
(A88) 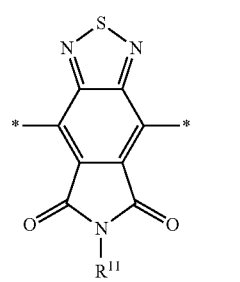
(A89) 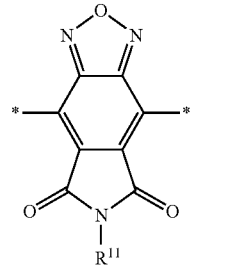
(A90) 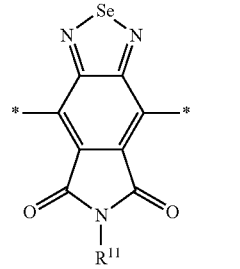
(A91) 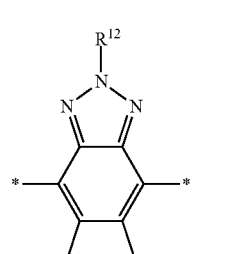

(A92) 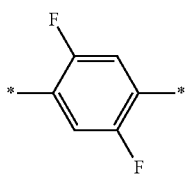

(A93) 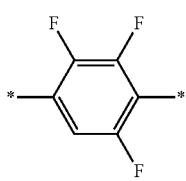

(A94) 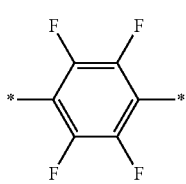

(A95) 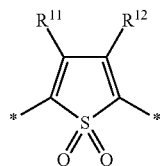

(A96) 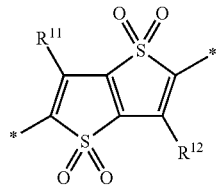

wherein $R^{11}$, $R^{12}$, $R^{13}$, $R^{14}$, $R^{15}$ and $R^{16}$ are independently of each other selected from the group consisting of H and $R^S$ as defined earlier.

The present tetra-aryl indacenodithiophenes may be synthesized using standard reactions. An exemplary synthesis is shown in Scheme 1, wherein O—R' is used to denote a leaving group, such as for example methoxy or ethoxy, and for reasons of simplicity Ar is used to denote $Ar^1$, $Ar^2$, $Ar^3$ and $Ar^4$, respectively.

Scheme 1

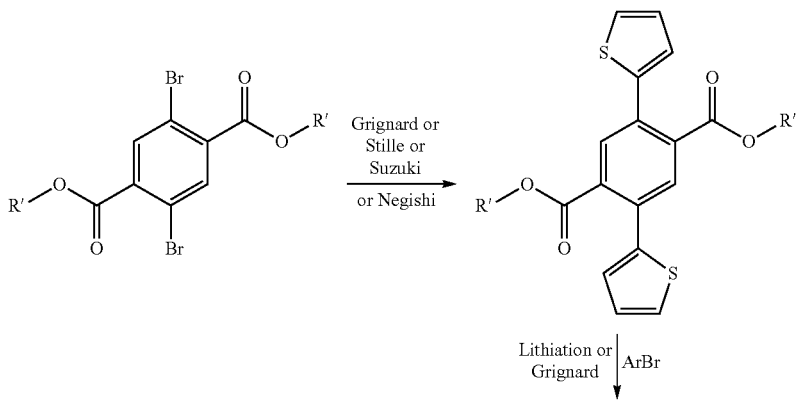

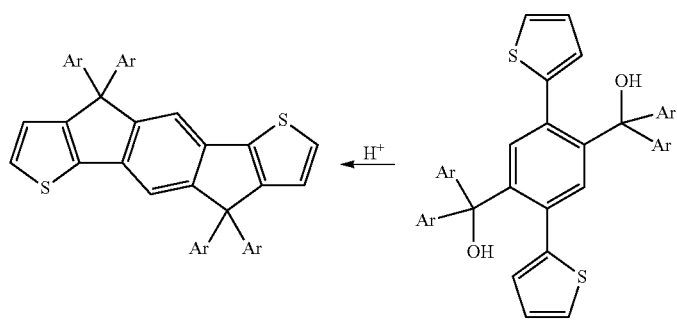

As specific examples of compounds of general formulae (I-a) and (I-b) mention may be made of the compounds of following formulae (Ex-A), (Ex-B) and (Ex-C) with $R^1$ and $Ar^5$ as defined herein.

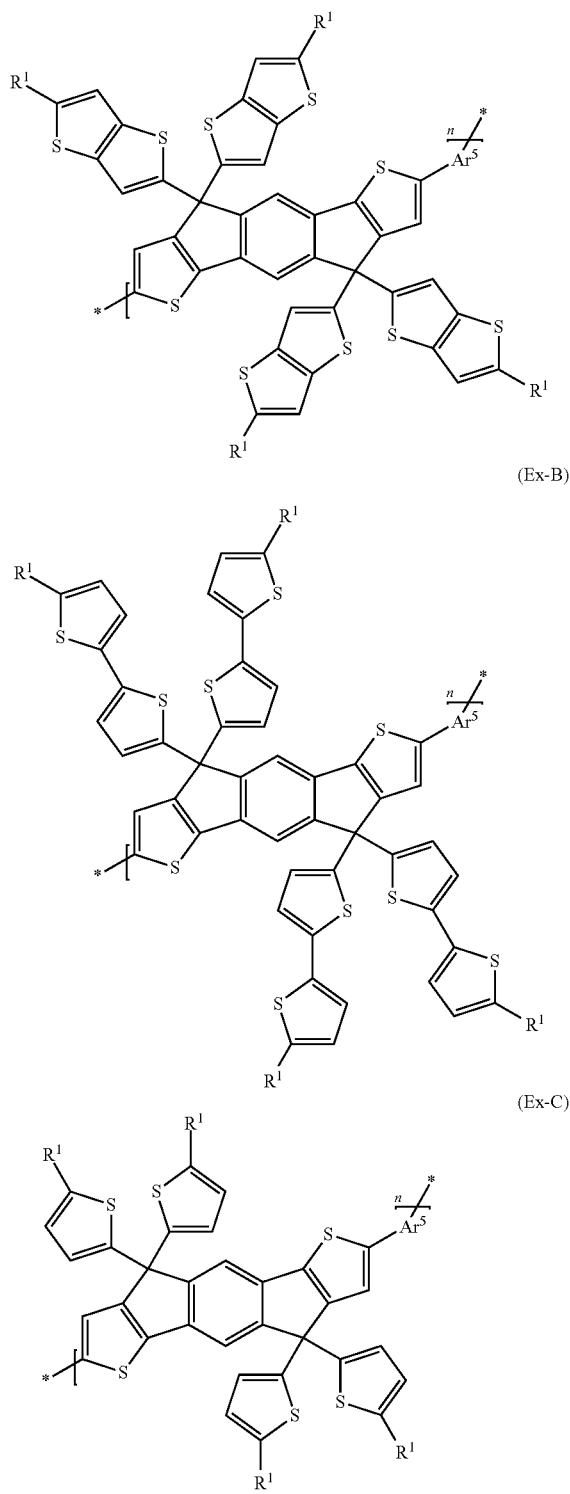

Of formulae (Ex-A), (Ex-B) and (Ex-C) those are preferred wherein $R^1$ is an alkyl having at least 1, preferably at least 5, more preferably at least 10 and most preferably at least 15 and/or has at most 40, more preferably at most 30, even more preferably at most 25 and most preferably at most 20 carbon atoms, and $Ar^5$ is selected from formulae (D10), preferably (D10) with $R^{11}=R^{12}=H$, (A1), preferably (A1) with $R^{11}=R^{12}=H$, and (D19), preferably (D19) $R^{11}=R^{12}=H$. Specific preferred examples are Polymer 1, Polymer 2 and Polymer 3 as shown in the examples.

Compounds comprising the structural unit of formulae (I-a) or (I-b) as defined above may preferably be selected from the group consisting of small molecules, monomers and polymers. As used herein, the term "small molecule" will be used to denote a compound comprising a structural unit of formula (I-a) or (I-b) and two inert chemical groups, which are inert under use condition and thus inhibit such a small molecule from reacting further, particularly from being polymerized. In contrast hereto, the term "monomer" is used to denote a compound comprising a structural unit of formula (I-a) or (I-b) and at least one reactive chemical group, which allows such monomer to be reacted, for example so as to form part of a polymer.

Small Molecule and Monomer

In one aspect the present application provides for a small molecule, i.e. for a compound comprising a structural unit of formula (I-a) or (I-b) and two inert chemical groups $R^a$ and $R^b$. Such a small molecule may for example be represented by formula (IV-a)

$$R^a\text{-}M^0\text{-}R^b \qquad \text{(IV-a)}$$

wherein $M^0$ comprises a structural unit M of formula (I-a) or (I-b) and $R^a$ and $R^b$ are inert chemical groups. Such inert chemical groups $R^a$ and $R^b$ may independently of each other for example be chosen from the group consisting of hydrogen, fluorine, alkyl having from 1 to 10 carbon atoms, fluoroalkyl having from 1 to 10 carbon atoms, aromatic ring systems of from 5 to 30 carbon atoms and aromatic ring systems of from 5 to 30 carbon atoms wherein one or more hydrogen atom may independently of each other be replaced by fluorine or alkyl having from 1 to 10 carbon atoms.

In another aspect the present application provides for a monomer, i.e. for a compound comprising a structural unit of formula (I-a) or (I-b) and at least one reactive chemical group $R^c$ which may be selected from the group consisting of Cl, Br, I, O-tosylate, O-triflate, O-mesylate, O-nonaflate, —SiMe$_2$F, —SiMeF$_2$, —O—SO$_2Z^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, preferably —B(OZ$^2$)$_2$ or —Sn(Z$^4$)$_3$, wherein $X^0$ is as defined above, and $Z^1$, $Z^2$, $Z^3$ and $Z^4$ are selected from the group consisting of alkyl and aryl, preferably alkyl having from 1 to 10 carbon atoms, each being optionally substituted with $R^0$ as defined above, and two groups $Z^2$ may also together form a cyclic group. Alternatively such a monomer may comprise two reactive chemical groups and is for example represented by formula (IV-b)

$$R^c\text{-}M^0\text{-}R^d \qquad \text{(IV-b)}$$

wherein $M^0$ comprises a structural M unit of formula (I-a) or (I-b) and $R^c$ and $R^d$ are reactive chemical groups as defined above for $R^c$.

Preferably, $M^0$ in formulae (IV-a) and (IV-b) may further comprise one or more (for example 2, 3, 4, 5, 6, 7, 8, 9 or 10) aryl or heteroaryl as defined above. Preferred examples of $M^0$ may comprise, preferably consist of, the following $$*\text{—}U^a_{m1}\text{—}Ar^a_{m2}\text{—}U^b_{m3}\text{—}Ar^b_{m4}\text{—}Ar^c_{m5}\text{—}* \qquad \text{(V)}$$

wherein

U$^a$ and U$^b$ are independently of each other selected from the structural unit M of formula (I-a), (I-b) and any of its subformulae as defined above;

Ar$^a$, Ar$^b$ and Ar$^c$ are independently of each other selected as defined for Ar$^5$;

m1, m2, m3 and m4 are independently of each other selected from the group consisting of 0, 1 and 2, with the provision that at least one of m1 and m3 is not 0; and m5 is 0 or an integer from 1 to 10 (for example 1, 2, 3, 4, 5, 6, 7, 8, 9 or 10).

Preferred small molecules and monomers are those with M$^0$ selected from one of the following formula (V-a-1) and (V-a-2)

  (V-a-1)

  (V-a-2)

with Ar$^a$, Ar$^b$, U$^a$, U$^b$, m1, m2, m3 and m4 as defined above.

*—U$^a$—Ar$^b$—*  (V-b-4)

*—U$^a$—Ar$^a$—U$^b$—*  (V-b-5)

with Ar$^a$, Ar$^b$, U$^a$ and U$^b$ as defined above.

Particularly preferred examples of M$^0$ of formulae (V), (V-a-1), (V-a-2) and (V-b-1) to (V-b-5) are those wherein one or more of Ar$^a$, Ar$^b$ and Ar$^c$ is/are selected from the group consisting of arylene or heteroarylene having electron donor properties and arylene or heteroarylene having electron acceptor properties as defined in respect to Ar$^5$.

The monomers of the present invention may be synthesized by generally known reactions, such as for example lithiation followed by reaction with a reagent that supplies the respective functional groups. Examples of such reactions are indicated in Scheme 2, wherein O—R' is used to denote a leaving group, such as for example methoxy or ethoxy, R' correspondingly denotes for example an alkyl group, such as for example methyl or ethyl, and for reasons of simplicity Ar is used to denote Ar$^1$, Ar$^2$, Ar$^3$ and Ar$^4$, respectively.

Scheme 2

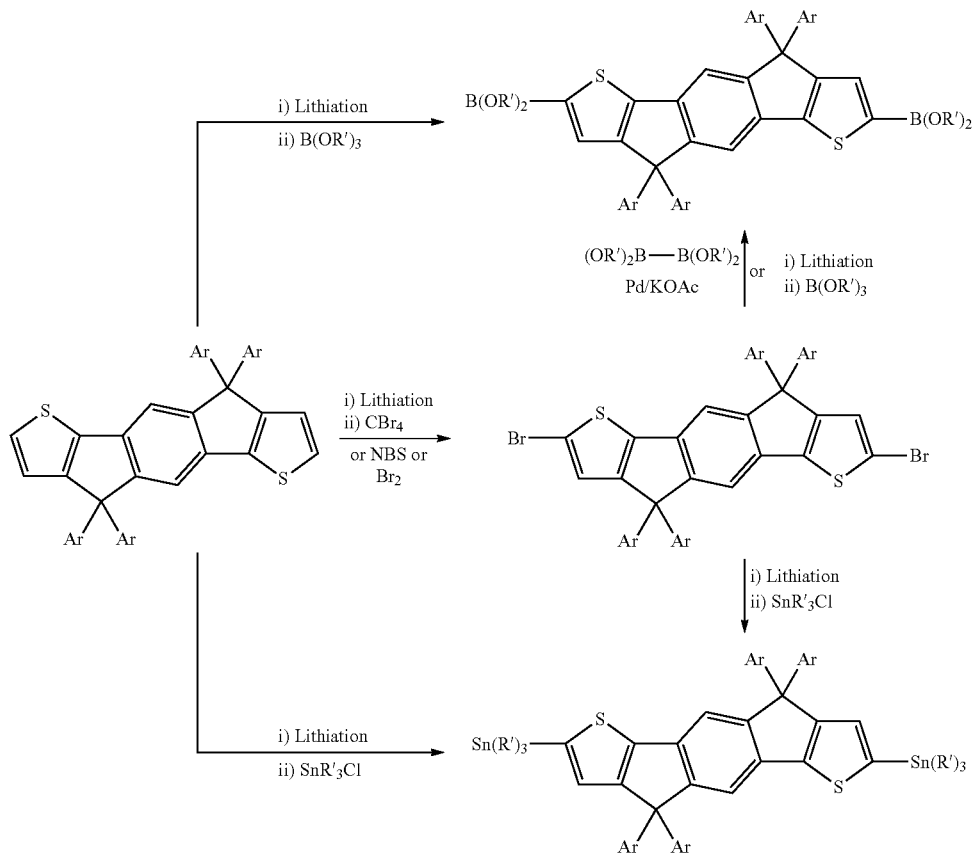

Especially preferred small molecules and monomers are those with M$^0$ selected from one of the following formulae (V-b-1) to (V-b-5)

  (V-b-1)

*—U$^a$—*  (V-b-2)

  (V-b-3)

Polymer

In a further aspect the present application provides for an oligomer or polymer, i.e. for a compound comprising more than one structural unit of formula (I-a) or (I-b). Preferably such oligomer or polymer comprises more than one group M$^0$ as defined in any one of formulae (V), (V-a-1), (V-a-2) and (V-b-1) to (V-b-5). At each occurrence M$^0$ may be the same or different.

Optionally, such oligomer or polymer may further comprise a repeating unit comprising a group selected from monocyclic or polycyclic aryl or heteroaryl groups that are unsubstituted or substituted with one or more groups $R^S$. Preferably such further repeating units are selected from one of the following

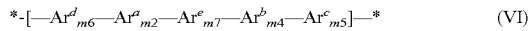 (VI)

wherein $Ar^a$, $Ar^b$, $Ar^c$, $Ar^d$ and $Ar^e$ are independently of each other selected as defined for $Ar^5$; and m2, m4, m5, m6 and m7 are independently of each other 0, 1 or 2, provided that at least one of m6 and m7 is not 0 (for example m6 is 0 and m7 is 1, or m6 is 1 and m7 is 0, or m6 is 1 and m7 is 1).

Preferred oligomers and polymers may for example comprise a polymer chain of formula (VII)

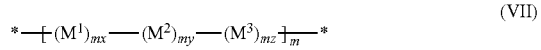 (VII)

wherein m is an integer>1;

$M^1$, $M^2$ and $M^3$ are independently of each other monomeric units as defined below, provided that at least one of $M^1$, $M^2$ and $M^3$ comprises a structural unit M of formula (I-a) or (I-b);

mx is >0 and ≤1;

my is ≥2 and <1; and mz is ≥0 and <1, with the provision that mx+my+mz=1 and with the provision that for whichever of $M^1$, $M^2$ or $M^3$ comprises the structural unit M of formula (I-a) or (I-b) the respective mx, my or mz is >0. Thus, if M is comprised in $M^2$, then my>0, and if M is comprised in $M^3$, then mz>0.

Preferably, each unit $*-(M^1)_{mx}-(M^2)_{my}-(M^3)_{mz}-*$ of the polymer chain of formula (VII) comprises at least one unit of structural formula M of formula (I-a) or formula (I-b).

Preferably $M^1$, $M^2$ and $M^3$ are independently of each other selected from the group consisting of $M^0$ as defined in and for above formulae (V), (V-a-1), (V-a-2) and (V-b-1) to (V-b-5).

Examples of suitable polymer chains of formula (VI) may be selected from the following formulae (VII-1) to (VII-10)

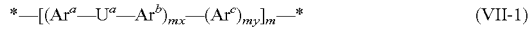 (VII-1)

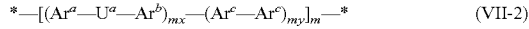 (VII-2)

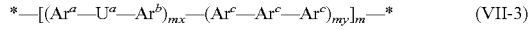 (VII-3)

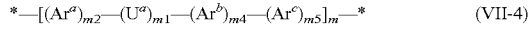 (VII-4)

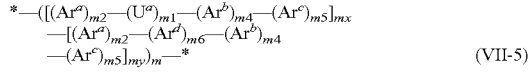 (VII-5)

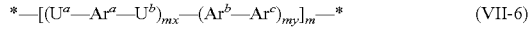 (VII-6)

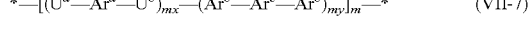 (VII-7)

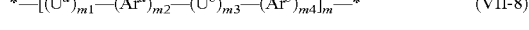 (VII-8)

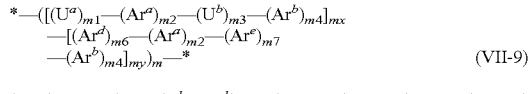 (VII-9)

 (VII-10)

wherein $Ar^a$, $Ar^b$, $Ar^c$, $Ar^d$, $Ar^e$, $U^a$, $U^b$, m1, m2, m3, m4, m5, m6, m7, m, mx, my and mz are as defined above, and $U^c$ is as defined above for $U^a$ and $U^b$.

The present oligomers and polymers include homopolymers and copolymers, such as for example statistical or random copolymers, alternating copolymers and block copolymers as well as any combination of these.

Such polymers can be alternating or random copolymers. With respect to formulae (VII-4) and (VII-6) it is preferred that in at least one of the repeating units $[(Ar^a)_{m2}-(U^a)_{m1}-(Ar^b)_{m4}-(Ar^c)_{m5}]$, and—if present—in at least one of the repeating units $[(Ar^a)_{m2}-(Ar^d)_{m6}-(Ar^b)_{m4}-(Ar^c)_{m5}]$ m1 is at least 1 and m4 is at least 1. With respect to formulae (VII-8) and (VII-9) it is preferred that in at least one of the repeating units $[(U^a)_{m1}-(Ar^a)_{m2}-(U^b)_{m3}-(Ar^b)_{m4}]$, and—if present—in at least one of the repeating units $[(Ar^d)_{m6}-(Ar^a)_{m2}-(Ar^e)_{m7}-(Ar^b)_{m4}]$ m1 is at least 1 and m6 is at least 1.

For the present oligomers and polymers the total number m of repeating units is preferably from 2 to 10000. For a polymer the total number m of repeating units is preferably at least 10 and most preferably at least 50. For a polymer the total number m of repeating units is preferably at most 2000, more preferably at most 1000 and most preferably at most 500. Any combination of these values is also possible.

Particularly preferred are polymers selected from the following groups a) Group 1 consisting of homopolymers of the unit $U^a$ or $(Ar^a-U^a)$ or $(Ar^a-U^a-Ar^b)$ or $(Ar^a-U^a-Ar^c)$ or $(U^a-Ar^b-Ar^c)$ or $(Ar^a-U^a-Ar^b-Ar^c)$ or $(U^a-Ar^a-U^a)$, i.e. where all repeating units are identical, whereby it is noted that a polymer consisting of units $(Ar^a-U^a)$ could also be seen as an alternating copolymer depending on the respective view of the monomeric unit, b) Group 2 consisting of random or alternating copolymers formed by identical units $(Ar^a-U^a-Ar^b)$ or $(U^a-Ar^a-U^a)$ and identical units $(Ar^c)$, c) Group 3 consisting of random or alternating copolymers formed by identical units $(Ar^a-U^a-Ar^b)$ or $(U^a-Ar^a-U^b)$ and identical units $(Ar^a)$, d) Group 4 consisting of random or alternating copolymers formed by identical units $(Ar^a-U^a-Ar^b)$ or $(U^a-Ar^a-U^b)$ and identical units $(Ar^a-Ar^d-Ar^b)$ or $(Ar^d-Ar^a-Ar^e)$, wherein in all these groups $Ar^a$, $Ar^b$, $Ar^c$, $Ar^d$, $Ar^e$, $U^a$ and $U^b$ are as defined above and below, in groups 1, 2 and 3 $Ar^a$, $Ar^b$ and $Ar^c$ are different from a single bond, and in group 4 one of $Ar^a$ and $Ar^b$ may also denote a single bond.

Preferred polymers of formulae (VII) and (VII-1) to (VII-10) may be those of formula (VIII)

$R^e$-chain-$R^f$ (VIII)

wherein "chain" denotes a polymer chain of any one of formulae (VII) or (VII-1) to (VII-10), and $R^e$ and $R^f$ have independently of each other one of the meanings of $R^S$ as defined above, or denote, independently of each other, H, F, Br, Cl, I, $-CH_2Cl$, $-CHO$, $-CR^O=CR^{OO}{}_2$, $-SiR^OR^{OO}R^{OOO}$, $-SiR^OX''X'''$, $-SiR^OR^{OO}X''$, $-SnR^OR^{OO}R^{OOO}$, $-BR^OR^{OO}$, $-B(OR^O)(OR^O)$, $-B(OH)_2$, $-O-SO_2-R^O$, $-C\equiv CH$, $-C\equiv C-SiR^O{}_3$, $-ZnX''$ or an endcap group, X'' and X''' denote halogen, $R^O$, $R^{OO}$ and $R^{OOO}$ are as defined earlier, and two of $R^O$, $R^{OO}$ and $R^{OOO}$ may also form a ring together with the atom to which they are attached.

Preferred endcap groups $R^e$ and $R^f$ may be selected from the group consisting of H, alkyl having from 1 to 20 carbon atoms, aryl having from 6 to 12 carbon atoms and heteroaryl having from 5 to 10 aromatic ring atoms, said aryl and heteroaryl being unsubstituted or substituted with one or more groups $R^S$. More preferred endcap groups $R^e$ and $R^f$ may be selected from the group consisting of H, alkyl having from 1 to 10 carbon atoms and phenyl.

In the polymer chains of formulae (VII) and (VII-1) to (VII-10) mx, my and mz denote the mole fraction of units $M^1$, $M^2$ and $M^3$, respectively, and m denotes the degree of polymerisation. These formulae are intended to include block copolymers, random or statistical copolymers and alternating copolymers of $M^1$, $M^2$ and $M^3$, as well as homopolymers of $M^1$ for the case when mx>0 and my=mz =0.

Further preferred are repeating units, monomers, oligomers and polymers of formulae (IV-a), (IV-b), (V), (V-a-1), (V-a-2), (V-b-1) to (V-b-5), (VI), (VII), (VII-1) to (VII-10) and (VIII) characterised by one or more of the following preferred or alternative aspects provided that such aspects are not mutually exclusive:

0<my<1 and mz=0;
0<my<1 and 0<mz<1;
$M_w$ is at least 5,000, preferably at least 8,000, more preferably at least 10,000;
$M_w$ is at most 300,000, preferably at most 100,000;
$R^e$ and $R^f$ are independently of each other selected from H, halogen, —$CH_2Cl$, —CHO, —CH=$CH_2$— $SiR^{00}R^0R^{000}$, —$SnR^0R^{00}R^{000}$, —$BR^0R^0$, —$B(OR^0)(OR^0)$, —$B(OH)_2$, $C_1$-$C_{20}$-alkyl, $C_1$-$C_{20}$-alkoxy, $C_2$-$C_{20}$-alkenyl, $C_1$-$C_{20}$-fluoroalkyl, aryl (preferably phenyl) and heteroaryl, said aryl and heteroaryl being unsubstituted or substituted with one or more groups $R^S$.
$R^c$ and $R^d$ are independently of each other selected from the group consisting of Cl, Br, I, O-tosylate, O-triflate, O-mesylate, O-nonaflate, —$SiMe_2F$, —$SiMeF_2$, —O—$SO_2Z^1$, —$B(OZ^2)_2$, —$CZ^3$=$C(Z^4)_2$, —C≡CH, C≡$CSi(Z^1)_3$, —$ZnX^0$ and —$Sn(Z^4)_3$, wherein $X^0$ is halogen, and $Z^1$, $Z^2$, $Z^3$ and $Z^4$ are selected from the group consisting of alkyl and aryl, each being unsubstituted or substituted with one or more groups $R^S$, and two groups $Z^2$ may also form a cyclic group.

A particularly preferred polymer is of the following formula (III-a)

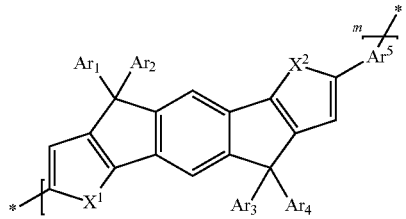
(III-a)

with $X^1$, $X^2$, $Ar^1$, $Ar^2$, $Ar^3$, $Ar^4$, $Ar^5$ and m as defined above.

The compounds of the present invention can be synthesized according to or in analogy to methods that are known to the skilled person and are described in the literature. Other methods of preparation can be taken from the examples. For example, the polymers can be suitably prepared by aryl-aryl coupling reactions, such as Yamamoto coupling, Suzuki coupling, Stille coupling, Sonogashira coupling, Heck coupling, Negishi coupling, C—H activation coupling or Buchwald coupling. Suzuki coupling, Stille coupling and Yamamoto coupling are especially preferred. The monomers which are polymerized to form the repeat units of the polymers can be prepared according to methods which are known to the person skilled in the art.

Thus, the process for preparing the present polymers comprises the step of coupling monomers, therein comprised a monomer comprising the structural unit of formula (I-a) or (I-b), said monomers comprising at least one or alternatively two functional monovalent group selected from the group consisting of Cl, Br, I, O-tosylate, O-triflate, O-mesylate, O-nonaflate, —$SiMe_2F$, —$SiMeF_2$, —O—$SO_2Z^1$, —$B(OZ^2)_2$, —$CZ^3$=$C(Z^3)_2$, —C≡CH, —C≡$CSi(Z^1)_3$, —$ZnX^0$ and —$Sn(Z^4)_3$, wherein $X^0$ is halogen, and $Z^1$, $Z^2$, $Z^3$ and $Z^4$ are independently of each other selected from the group consisting of alkyl and aryl, each being optionally substituted with one or more groups $R^0$ as defined herein, and two groups $Z^2$ may also together form a cyclic group.

Preferably the polymers are prepared from monomers of general formula (IV-b) or their preferred subformulae as described above and below.

Another aspect of the invention is a process for preparing a polymer by coupling one or more identical or different monomeric units comprising a structural unit of formula (I-a) or (I-b) or monomers of general formula (IV-a) with each other and/or with one or more co-monomers in a polymerisation reaction, preferably in an aryl-aryl coupling reaction.

Suitable and preferred comonomers may be selected from the following formulae $R^c$—$(Ar^a)_{m2}$—$Ar^d$—$(Ar^b)_{m4}R^d$      (IX-1)

$R^c$—$Ar^a$—$R^d$      (IX-2)

$R^c$—$Ar^d$—$R^d$      (IX-3)

wherein $Ar^a$, $Ar^b$, $Ar^d$, m2, m4, $R^c$ and $R^d$ are as defined herein.

Very preferred is a process for preparing a polymer by coupling one or more monomers selected from formula (V-a-1) or (V-a-2) with one or more monomers of formula (IX-1), and optionally with one or more monomers selected from formula (IX-2) and (IX-3), in an aryl-aryl coupling reaction, wherein preferably $R^c$ and $R^d$ are selected from Cl, Br, I, —$B(OZ^2)_2$ and —$Sn(Z^4)_3$.

For example, preferred embodiments of the present invention relate to a) a process of preparing a polymer by coupling a monomer of formula (IX-1)

$R^c$—$Ar^a$—$U^a$—$Ar^b$—$R^d$ with a monomer of formula (IX-2)

$R^c$—$Ar^a$—$R^d$      (IX-2)

in an aryl-aryl coupling reaction; or b) a process of preparing a polymer by coupling a monomer of formula $R^c$—$U^a$—$R^d$ with a monomer of formula (IX-1)

$R^c$—$Ar^a$—$Ar^d$—$Ar^b$—$R^d$      (IX-1)

in an aryl-aryl coupling reaction; or c) a process of preparing a polymer by coupling a monomer of formula $R^c$—$U^a$—$R^d$ with a monomer of formula (IX-3)

$R^c$—$Ar^d$—$R^d$      (IX-3)

in an aryl-aryl coupling reaction; or d) a process of preparing a polymer by coupling a monomer of formula $R^c$—$U^a$—$R^d$ with a monomer of formula (IX-3)

$$R^c—Ar^d—R^d \quad \text{(IX-3)}$$

and a monomer of formula (IX-2)

$$R^c—Ar^a—R^d \quad \text{(IX-2)}$$

in an aryl-aryl coupling reaction; or
e) a process of preparing a polymer by coupling a monomer of formula $$R^c—U^a—Ar^a—U^b—R^d$$

with a monomer of formula (IX-2)

$$R^c—Ar^a—R^d \quad \text{(IX-2)}$$

in an aryl-aryl coupling reaction; or
f) a process of preparing a polymer by coupling a monomer of formula $$R^c—U^a—R^d$$

with a monomer of formula (IX-2)

$$R^c—Ar^a—R^d \quad \text{(IX-2)}$$

and a monomer of formula (IX-3)

$$R^c—Ar^d—R^d \quad \text{(IX-3)}$$

in an aryl-aryl coupling reaction,
wherein $Ar^a$, $Ar^b$, $Ar^d$, $U^a$, $U^b$, $R^c$ and $R^d$ are as defined herein, with $R^c$ and $R^d$ preferably selected from Cl, Br, I, $—B(OZ^2)_2$ and $—Sn(Z^4)_3$ as defined in respect to formulae (VI-a) and (IV-b).

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described for example in T. Yamamoto et al., *Prog. Polym. Sci.*, 1993, 17, 1153-1205, or WO 2004/022626 A1, and Stille coupling is described for example in Z. Bao et al., *J. Am. Chem. Soc.*, 1995, 117, 12426-12435. For example, when using Yamamoto coupling, monomers having two reactive halide groups are preferably used. When using Suzuki coupling, compounds of formula (IV-b) having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand, for example $Pd(Ph_3P)_4$. Another preferred phosphine ligand is tris(ortho-tolyl)phosphine, for example $Pd(o-Tol_3P)_4$. Preferred Pd(II) salts include palladium acetate, for example $Pd(OAc)_2$. Alternatively the Pd(0) complex can be prepared by mixing a Pd(0) dibenzylideneacetone complex, for example tris(dibenzyl-idenecacetone) dipalladium(0), bis(dibenzylideneacetone)-palladium(0), or Pd(II) salts e.g. palladium acetate, with a phosphine ligand, for example triphenylphosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl)nickel(0).

Suzuki and Stille polymerisation may be used to prepare homopolymers as well as statistical, alternating and block random copolymers. Statistical or block copolymers can be prepared for example from the above monomers of formula (VI) or its subformulae, wherein one of the reactive groups is halogen and the other reactive group is a boronic acid, boronic acid derivative group or and alkylstannane. The synthesis of statistical, alternating and block copolymers is described in detail for example in WO 03/048225 A2 or WO 2005/014688 A2.

As alternatives to halogens as described above, leaving groups of formula $—O—SO_2Z^1$ can be used wherein $Z^1$ is as described above. Particular examples of such leaving groups are tosylate, mesylate and triflate.

Schematic representations of examples for the production of (homo)polymers are shown in Scheme 3, wherein for reasons of simplicity Ar is used to denote $Ar^1$, $Ar^2$, $Ar^3$ and $Ar^4$, respectively.

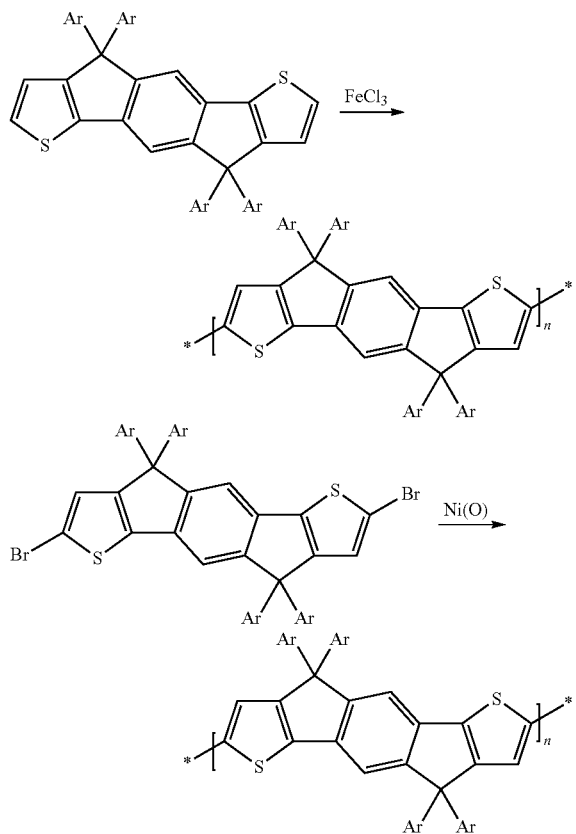

Scheme 3

Blends, Formulations and Devices

The compounds and polymers according to the present invention can also be used in mixtures or polymer blends, for example together with small molecules or monomeric compounds or together with other polymers having charge-transport, semiconducting, electrically conducting, photo-conducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more small molecules, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluoro-toluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, tetraline, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight, with % by weight given relative to the total weight of the solution. Optionally, the solution also comprises one or more binders to adjust the rheological properties, as described for example in WO 2005/055248 A1.

After appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in J. D. Crowley et al., *Journal of Paint Technology*, 1966, 38 (496), 296. Solvent blends may also be used and can be identified as described in Solvents, W. H. Ellis, Federation of Societies for Coatings Technology, p. 9-10, 1986. Such a procedure may lead to a blend of 'non'-solvents that will dissolve both the polymers of the present invention, although it is desirable to have at least one true solvent in a blend.

The compounds and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices need to be prepared. Selected formulations of the present invention may be applied to prefabricated device substrates by ink jet printing or microdispensing. Preferably industrial piezoelectric print heads such as but not limited to those supplied by Aprion, Hitachi-Koki, Inkjet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points>100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point>100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds and polymers to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting compound, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a compound, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a compound, polymer, polymer blend, formulation or organic semiconducting layer according to the present invention. Preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns. Particularly preferred devices are OLEDs.

Especially preferred electronic device are OFETs, OLEDs, OPV and OPD devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide ($ZnO_x$), zinc tin oxide (ZTO), titan oxide ($TiO_x$), molybdenum oxide ($MoO_x$), nickel oxide ($NiO_x$), or cadmium selenide (CdSe), or an organic material such as graphene or a fullerene or a substituted fullerene, for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.* 2004, 16, 4533).

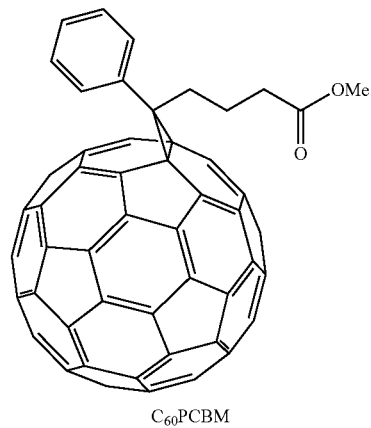 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

Preferably the polymer according to the present invention is blended with an n-type semiconductor such as a fullerene or substituted fullerene, like for example PCBM-$C_{60}$, PCBM-$C_{70}$, PCBM-$C_{61}$, PCBM-$C_{71}$, bis-PCBM-$C_{61}$, bis-PCBM-$C_{71}$, ICMA-$c_{60}$ (1',4'-Dihydro-naphtho[2',3':1,2][5,6]fullerene-$C_{60}$), ICBA-$C_{60}$, oQDM-$C_{60}$ (1',4'-dihydro-naphtho[2', 3':1,9][5,6]fullerene-C60-lh), bis-oQDM-$C_{60}$, graphene, or a metal oxide, like for example, $ZnO_x$, $TiO_x$, ZTO, $MoO_x$, $NiO_x$, or quantum dots like for example CdSe or CdS, to form the active layer in an OPV or OPD device. The device preferably further comprises a first transparent or semi-transparent electrode on a transparent or semi-transparent substrate on one side of the active layer, and a second metallic or semi-transparent electrode on the other side of the active layer.

Further preferably the OPV or OPD device comprises, between the active layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly[(9,9-bis(2-ethylhexyl)-fluorene]-b-poly[3-(6-trimethylammonium-hexyl)thiophene], or poly[(9,9-bis(3'-(N,N-dimethyl-amino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a blend or mixture of a polymer according to the present invention with a fullerene or modified fullerene, the ratio polymer:fullerene is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a $C_{60}$ or $C_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.,* 2006, 89, 233517).

A first preferred OPV device according to the invention comprises the following layers (in the sequence from bottom to top):

optionally a substrate,
a high work function electrode, preferably comprising a metal oxide, like for example ITO, serving as anode,
an optional conducting polymer layer or hole transport layer, preferably comprising an organic poymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1, 1'biphenyl-4,4'-diamine) or NBD (N,N'-dyphenyl-N—N'-bis(1-napthylphenyl)-1,1'biphenyl-4,4'-diamine),
a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF,
a low work function electrode, preferably comprising a metal like for example aluminum, serving as cathode,
wherein at least one of the electrodes, preferably the anode, is transparent to visible light, and
wherein the p-type semiconductor is a polymer according to the present invention.

A second preferred OPV device according to the invention is an inverted OPV device and comprises the following layers (in the sequence from bottom to top):
optionally a substrate,
a high work function metal or metal oxide electrode, comprising for example ITO, serving as cathode,
a layer having hole blocking properties, preferably comprising a metal oxide like $TiO_x$ or $Zn_x$,
an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic polymer or polymer blend, for example of PEDOT:PSS or TBD or NBD,
an electrode comprising a high work function metal like for example silver, serving as anode,
wherein at least one of the electrodes, preferably the cathode, is transparent to visible light, and
wherein the p-type semiconductor is a polymer according to the present invention.

In the OPV devices of the present invention the p-type and n-type semiconductor materials are preferably selected from the materials, like the polymer/fullerene systems, as described above When the active layer is deposited on the substrate, it forms a BHJ that phase separates at nanoscale level. For discussion on nanoscale phase separation see Dennler et al, *Proceedings of the IEEE,* 2005, 93 (8), 1429 or Hoppe et al, *Adv. Func. Mater,* 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

The compounds, polymers, formulations and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound, polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers, and
 optionally a substrate,
wherein the semiconductor layer preferably comprises a compound, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science*, 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, H$_2$IrCl$_6$, La(NO$_3$)$_3$.6H$_2$O, FSO$_2$OOSO$_2$F, Eu, acetylcholine, R$_4$N$^+$, (R is an alkyl group), R$_4$P$^+$ (R is an alkyl group), R$_6$As$^+$ (R is an alkyl group), and R$_3$S$^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant E ("permittivity") refer to values taken at 20° C. and 1,000 Hz.

EXAMPLES

The following non-limiting examples further illustrate the advantages of the present invention.

Example 1

2-Bromo-5-hexadecyl-thiophene

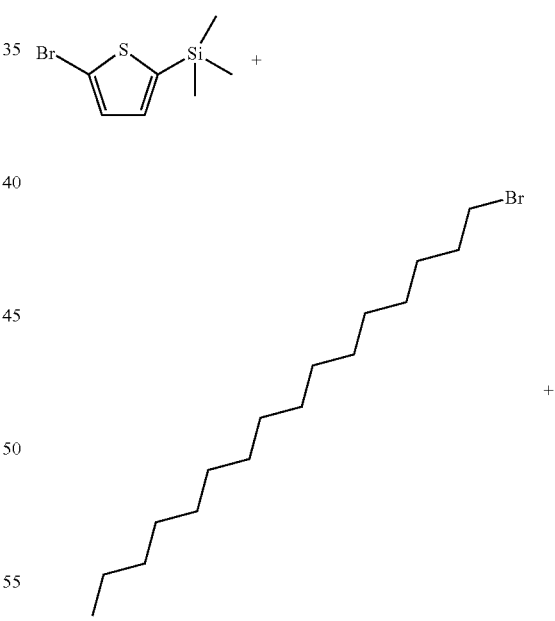

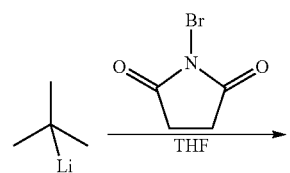

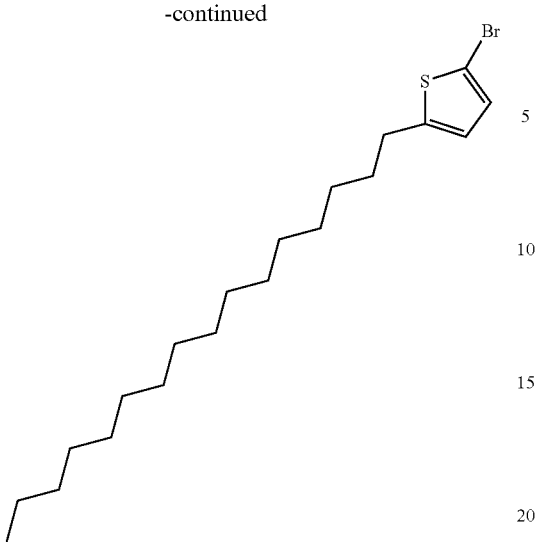

To a solution of (5-bromothiophen-2-yl)trimethylsilane (10.0 g, 42.5 mmol) in anhydrous tetrahydrofuran (150 cm³) at −78° C. was added dropwise tert-butyllithium (51.0 cm³, 86.7 mmol, 1.7 M in pentane) over 60 minutes. 1-Bromohexadecane (13.0 g, 42.5 mmol) was then added in one go. The mixture was then allowed to warm to 23° C. over 17 hours. The solvent was removed in vacuo, 40-60 petroleum ether (400 cm³) added and the mixture stirred at 23° C. for 30 minutes, filtered and the solvent removed in vacuo. The residue was taken up in N,N-dimethylformamide (150 cm³) and diethyl ether (50 cm³), followed by addition of 1-bromopyrrolidine-2,5-dione (9.1 g, 51 mmol) portion wise over 15 minutes. The resulting reaction mixture was stirred at 23° C. for 17 hours. Light petroleum ether (200 cm³) and water (200 cm³) was added and the mixture stirred at 23° C. for 30 minutes. The product was extracted with 40-60 petroleum ether (3×100 cm³). The combined organics were dried over anhydrous magnesium sulfate, filtered and the solvent removed in vacuo. The crude material was purified using silica gel column chromatography (40-60 petroleum ether) to give 2-bromo-5-hexadecylthiophene (12.1 g, 70%) as a clear oil.

¹H-NMR (300 MHz, CDCl₃) 0.85-0.96 (9H, s, CH₃), 1.23-1.34 (27H, m, CH₂), 1.60-1.69 (2H, m, CH₂), 2.70-2.78 (2H, m, CH₂), 6.54 (1H, d, ArH, J 3.6), 6.85 (1H, d, ArH, J 3.7).

2,5-Bis-(5-trimethylsilanyl-thiophen-2-yl)-terephthalic acid diethyl ester

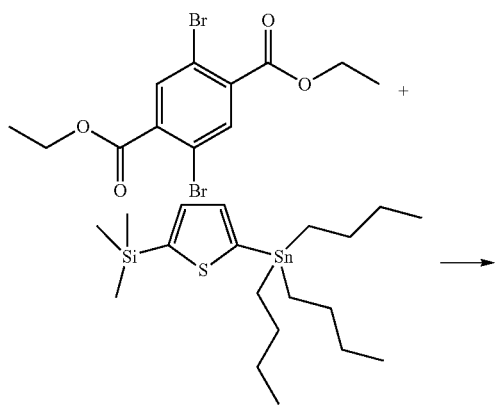

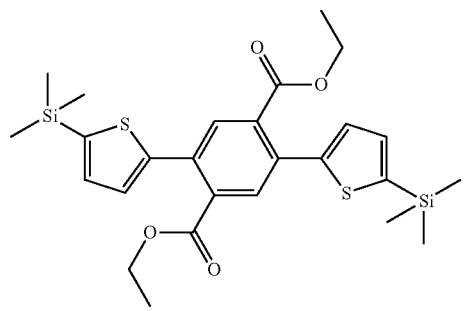

A mixture of 2,5-dibromo-terephthalic acid diethyl ester (6.8 g, 18.0 mmol), trimethyl-(5-tributylstannanyl-thiophen-2-yl)-silane (18.4 g, 41.4 mmol), tri-o-tolyl-phosphane (438 mg; 1.44 mmol) and anhydrous toluene (150 cm³) was degassed by nitrogen for 25 minutes. To the mixture was added tris(dibenzylideneacetone) dipalladium(0) (330 mg, 0.36 mmol) and the mixture further degassed for 15 minutes. The mixture was stirred at 100° C. for 17 hours and, after cooling to 23° C., the solvent removed in vacuo. The crude was purified using silica gel column chromatography (gradient from 40-60 petroleum ether to 40-60 petroleum ether: dichloromethane 4:6) to give 2,5-bis-(5-trimethylsilanyl-thiophen-2-yl)-terephthalic acid diethyl ester (5.9 g, 61%) as a white solid.

¹H-NMR (300 MHz, CDCl₃) 0.32-0.36 (18H, s, CH₃), 1.13 (6H, t, CH₃, J 7.2), 4.21 (4H, q, CH₂, J 7.2), 7.14 (2H, d, ArH, J 3.3), 7.20 (2H, d, ArH, J 3.3), 7.81 (2H, s, ArH).

4,9-Dihydro-4,4,9,9-tetrakis[5-(hexadecyl)thiophene]-s-5,10-dihydro-indaceno[1,2-b:5,6-b']dithiophene

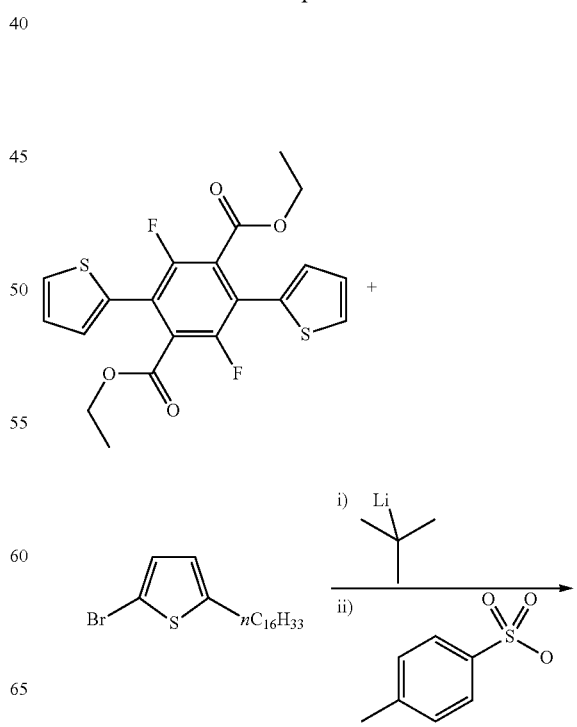

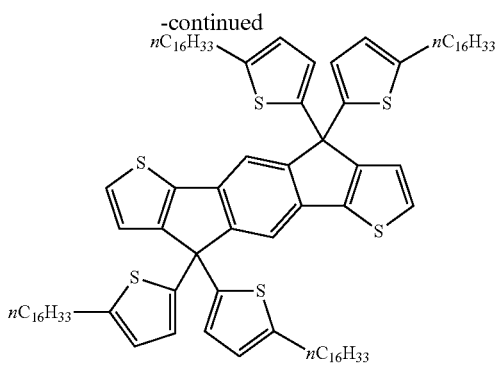
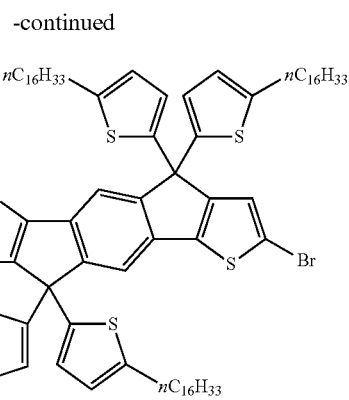

To a suspension of 2-bromo-5-hexadecylthiophene (7.9 g, 20 mmol) in anhydrous tetrahydrofuran (150 cm$^3$) at −78° C. was added dropwise tert-butyllithium (24.0 cm$^3$, 41.0 mmol, 1.7 M in pentane) over 35 minutes. After addition, the reaction mixture was stirred at −78° C. for 45 minutes. 2,5-Bis-(5-trimethylsilanyl-thiophen-2-yl)-terephthalic acid diethyl ester (1.8 mg, 3.4_mmol) was added in one go. The mixture was then allowed to warm to 23° C. over 17 hours. Water (200 cm$^3$) was added and the mixture stirred for 45 minutes. The product was extracted with diethyl ether (3×150 cm$^3$). The combined organics were dried over anhydrous magnesium sulfate, filtered and the solvent removed in vacuo. The residue was purified using silica gel column chromatography (gradient from 40-60 petroleum ether to 40-60 petroleum ether:dichloromethane 4:6) to give intermediate diol. To a solution of diol in anhydrous toluene (150 cm$^3$) was added p-toluenesulfonic acid (1.2 g, 6.8 mmol). The resulting solution was stirred at 70° C. for 3 hours. The reaction mixture was allowed to cool to 23° C. and the solvent removed in vacuo. The crude was purified using silica gel column chromatography (40-60 petroleum ether) to give 4,9-dihydro-4,4,9,9-tetrakis[5-(hexadecyl)thiophene]-s-5,10-dihydro-indaceno[1,2-b:5,6-b']dithiophene (720 mg, 14%) as a cream solid.

$^1$H-NMR (300 MHz, CDCl$_3$) 0.82-0.95 (12H, m, CH$_3$), 1.16-1.34 (104H, m, CH$_2$), 1.53-1.63 (8H, m, CH$_2$), 2.45-2.69 (8H, m, CH$_2$), 6.52 (2H, d, ArH, J 3.6), 6.70-6.78 (4H, m, ArH), 7.18 (2H, d, ArH, J 4.9), 7.29 (2H, d, ArH, J 5.0), 7.64 (2H, s, ArH).

2,7-Dibromo-4,9-dihydro-4,4,9,9-tetrakis[5-(hexadecyl)thiophene]-s-5,10-dihydro-indaceno[1,2-b:5,6-b']dithiophene 1-Bromo-pyrrolidine-2,5-dione (183 mg, 1.0 mmol) was added portion wise to a solution of 4,9-dihydro-4,4,9,9-tetrakis[5-(hexadecyl)thiophene]-s-5,10-dihydro-indaceno[1,2-b:5,6-b']dithiophene (700 mg, 0.47 mmol) in anhydrous tetrahydrofuran (30 cm$^3$) under a nitrogen atmosphere with absence of light at 0° C. After addition, the reaction mixture was stirred at 23° C. for 3 hours and then the reaction mixture was concentrated in vacuo. The residue was dissolved in 40-60 petroleum ether (20 cm$^3$) at 50° C. and purified using silica gel column chromatography (40-60 petroleum ether) to give 2,7-dibromo-4,9-dihydro-4,4,9,9-tetrakis[5-(hexadecyl)thiophene]-s-5,10-dihydro-indaceno[1,2-b:5,6-b']dithiophene (425 mg, 54.9%) as a pale cream crystalline solid.

$^1$H NMR (300 MHz, CDCl$_3$) 0.83-0.94 (12H, m, CH$_3$), 1.15-1.41 (104H, m, CH$_2$), 1.56-1.64 (8H, m, CH$_2$), 2.65-2.75 (8H, m, CH$_2$), 6.50-6.58 (4H, m, ArH), 6.65-6.70 (4H, m, ArH), 7.17 (2H, s, ArH), 7.53 (2H, s, ArH).

Polymer 1

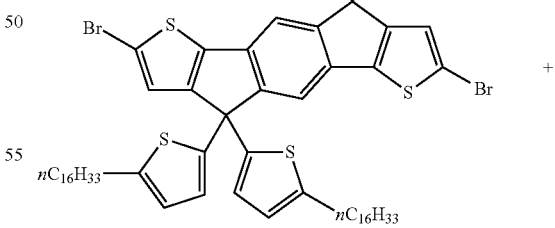

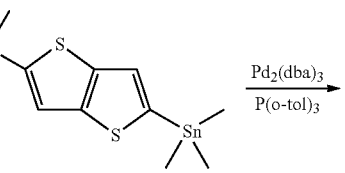

-continued

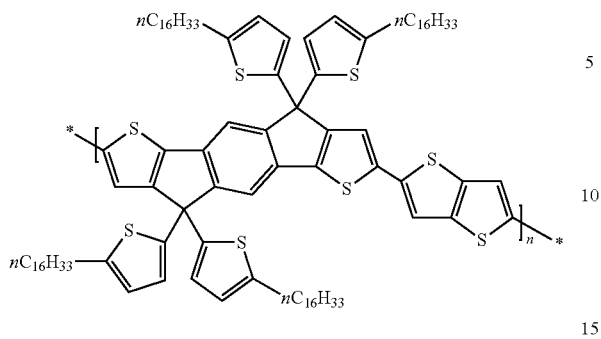

Nitrogen gas was bubbled through a mixture of 2,7-dibromo-4,9-dihydro-4,4,9,9-tetrakis[5-(hexadecyl)thiophene]-s-5,10-dihydro-indaceno[1,2-b:5,6-b']dithiophene (121 mg, 0.073 mmol), 2,5-thieno[3,2-b]thiophene (34.2 mg, 0.073 mmol), tri-o-tolyl-phosphine (7.4 mg, 0.024 mmol) and anhydrous toluene (4 cm³) for 30 minutes. Tris(dibenzylideneacetone)dipalladium(0) (4.6 mg, 0.007 mmol) was added and the reaction mixture heated in a pre-heated block at 100° C. for 30 minutes. Bromobenzene (0.03 cm³) was added and the mixture heated at 100° C. for 30 minutes before addition of tributyl-phenyl-stannane (0.08 cm³). The mixture was then heated at 100° C. for 1 hour. The mixture was allowed to cool slightly and poured into stirred methanol (200 cm³) and the polymer precipitate collected by filtration. The crude polymer was subjected to sequential soxhlet extraction with acetone, 40-60 petroleum ether and cyclohexanes. The cyclohexane extract was poured into methanol (400 cm³) and the polymer precipitate collected by filtration to give polymer 1 (106 mg, 89%) as a dark red solid.

GPC (chlorobenzene, 50° C.) $M_n$=76,000 g/mol, $M_w$=282,000 g/mol.

Example 2

Polymer 2

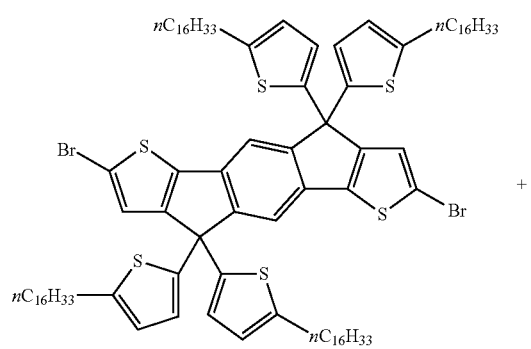

+

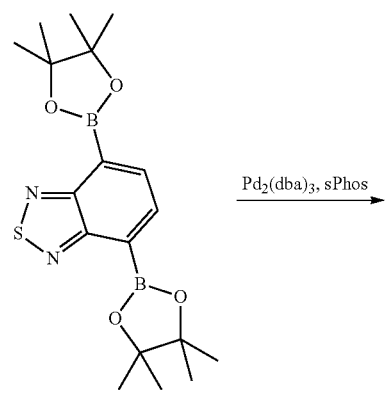

$\xrightarrow{Pd_2(dba)_3, sPhos}$

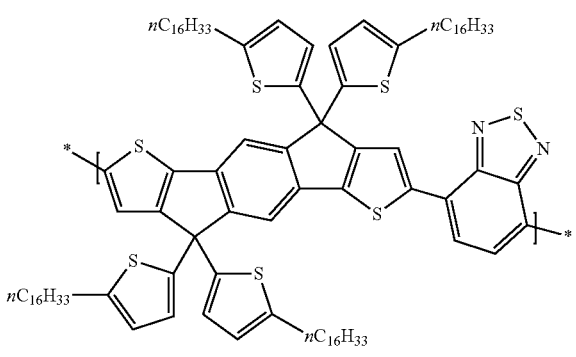

Nitrogen gas was bubbled through a mixture of 2,7-dibromo-4,9-dihydro-4,4,9,9-tetrakis[5-(hexadecyl)thiophene]-s-5,10-dihydro-indaceno[1,2-b:5,6-b']dithiophene (164 mg, 0.099 mmol), 4,7-bis-(4,4,5,5-tetramethyl-[1,3,2]dioxaborolan-2-yl)-benzo[1,2,5]thiadiazole (38.7 mg, 0.099 mmol), aliquat 336 (100 mg), 2-dicyclohexylphosphino-2',6'-dimethoxybiphenyl (18.6 mg, 0.045 mmol) and a solution of sodium carbonate (2 M aq., 1.0 cm³) in tetrahydrofuran (5 cm³) for 30 minutes. Tris(dibenzylideneacetone)dipalladium(0) (10.4 mg, 0.011 mmol) and toluene (5 cm³) were added and the reaction mixture was then heated in a pre-heated oil bath at 100° C. for 4 hours. Bromobenzene (0.02 cm³) was added and the mixture heated at 100° C. for 30 minutes before addition of phenylboronic acid (19 mg). The mixture was then heated at 100° C. for 1 hour. The mixture was allowed to cool slightly and poured into stirred methanol (200 cm³) and the polymer precipitate collected by filtration. The crude polymer was subjected to sequential soxhlet extraction with acetone, 40-60 petroleum ether and cyclohexanes. The cyclohexane extract was poured into methanol (400 cm³) and the polymer precipitate collected by filtration to give polymer 2 (124 mg, 77%) as a dark blue solid.

GPC (chlorobenzene, 50° C.) $M_n$=25,000 g/mol, $M_w$=54,000 g/mol.

Example 3

Polymer 3

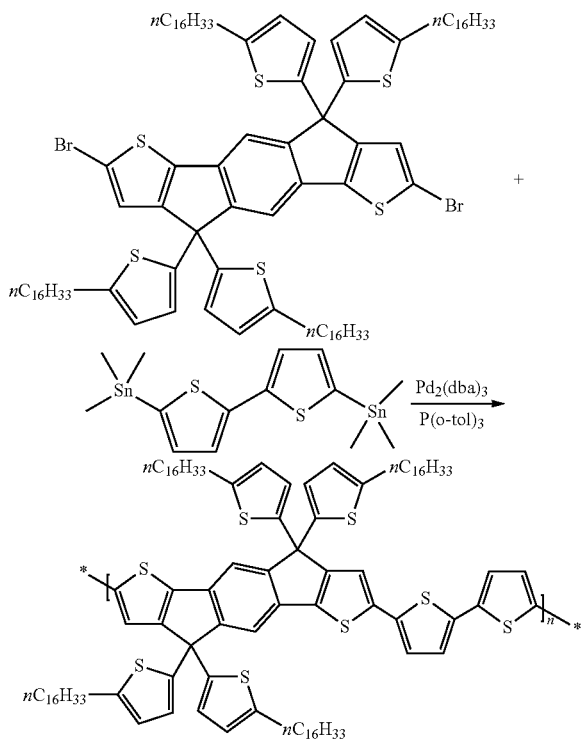

Nitrogen gas was bubbled through a mixture of 2,7-dibromo-4,9-dihydro-4,4,9,9-tetrakis[5-(hexadecyl)thiophene]-s-5,10-dihydro-indaceno[1,2-b:5,6-b']dithiophene (129 mg, 0.078 mmol), 5,5'-bis-trimethylstannanyl-[2,2'] bithiophenyl (38.4 mg, 0.078 mmol), tri-o-tolyl-phosphine (18.6 mg, 0.061 mmol) and anhydrous toluene (5 cm$^3$) for 30 minutes. Tris(dibenzylideneacetone)dipalladium(0) (10.4 mg, 0.011 mmol) was added and the reaction mixture heated in a pre-heated oil bath at 100° C. for 30 minutes. Bromobenzene (0.03 cm$^3$) was added and the mixture heated at 100° C. for 30 minutes before addition of tributyl-phenyl-stannane (0.08 cm$^3$). The mixture was then heated at 100° C. for 1 hour. The mixture was allowed to cool slightly and poured into stirred methanol (200 cm$^3$) and the polymer precipitate collected by filtration. The crude polymer was subjected to sequential soxhlet extraction with acetone, 40-60 petroleum ether and cyclohexanes. The cyclohexane extract was poured into methanol (400 cm$^3$) and the polymer precipitate collected by filtration to give polymer 3 (90 mg, 70%) as a dark red solid.

GPC (chlorobenzene, 50° C.) $M_n$=35,000 g/mol, $M_w$=84,000 g/mol.

Example 4

—Transistor Fabrication and Measurement

Top-gate thin-film organic field-effect transistors (OFETs) were fabricated on glass substrates with photolithographically defined Au source-drain electrodes. A 7 mg/cm$^3$ solution of the organic semiconductor in dichlorobenzene was spin-coated on top (an optional annealing of the film is carried out at 100° C., 150° C. or 200° C. for between 1 and 5 minutes) followed by a spin-coated fluoropolymer dielectric material (Lisicon® D139 from Merck, Germany). Finally a photolithographically defined Au gate electrode was deposited. The electrical characterization of the transistor devices was carried out in ambient air atmosphere using computer controlled Agilent 4155C Semiconductor Parameter Analyser. Charge carrier mobility in the saturation regime ($\mu_{sat}$) was calculated for the compound. Field-effect mobility was calculated in the saturation regime ($V_d$>($V_g$-$V_0$)) using equation (1):

$$\left(\frac{dI_d^{sat}}{dV_g}\right)_{V_d} = \frac{WC_i}{L}\mu^{sat}(V_g - V_0) \qquad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

The mobilities ($\mu_{sat}$) for polymers 1 and 3 in top-gate OFETs are summarized in Table 1.

TABLE 1

| Polymer | $\mu_{sat}$ [cm$^2$/Vs] |
|---------|-------------------------|
| 1       | 0.06                    |
| 3       | 0.03                    |

The invention claimed is:

1. A compound comprising at least one unit M of formula (I-a) and/or formula (I-b)

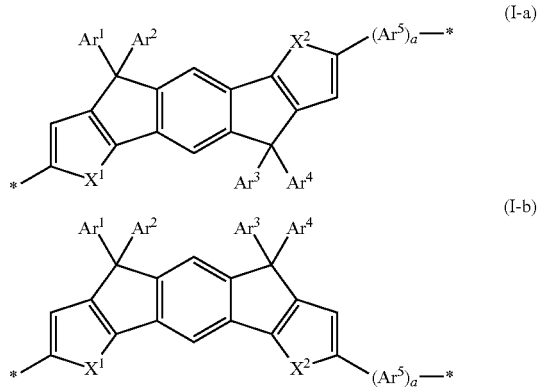

wherein $X^1$ and $X^2$ are independently of each other S or Se;

$Ar^1$, $Ar^2$, $Ar^3$ and $Ar^4$ are independently of each other heteroaryl having from 5 to 30 aromatic ring atoms, said heteroaryl being substituted with one or more groups $R^S$;

a is 0 or an integer from 1 to 10;

$Ar^5$ is at each occurrence independently —$CR^S$=$CR^S$—, —C≡C—, arylene having from 6 to 30 aromatic carbon atoms or heteroarylene having from 5 to 30 aromatic ring atoms, wherein said arylene or heteroarylene is unsubstituted or substituted with one or more groups $R^S$;

$R^S$ is at each occurrence independently alkyl having at least 1 and at most 40 carbon atoms.

2. The compound according to claim 1, wherein $X^1$ and $X^2$ are both S.
3. The compound according to claim 1, wherein M is of formula (I-a).
4. The compound according to claim 1, wherein $Ar^1$, $Ar^2$, $Ar^3$ and $Ar^4$ are independently of each other one of formulae (H-1) to (H-34)
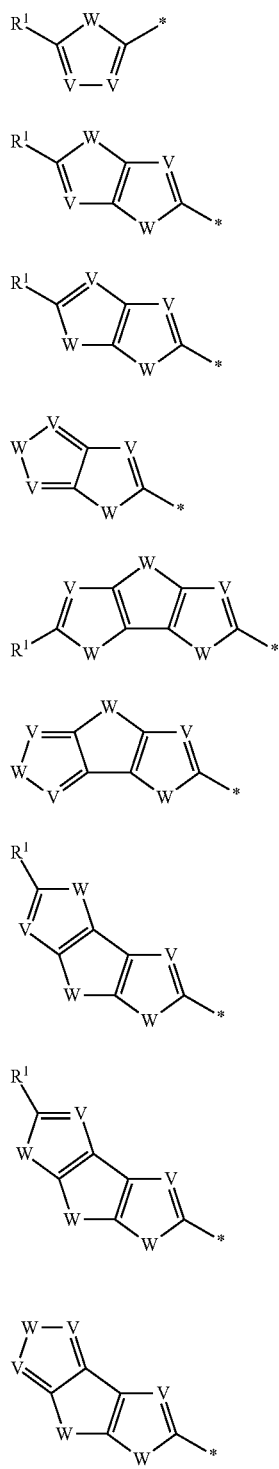
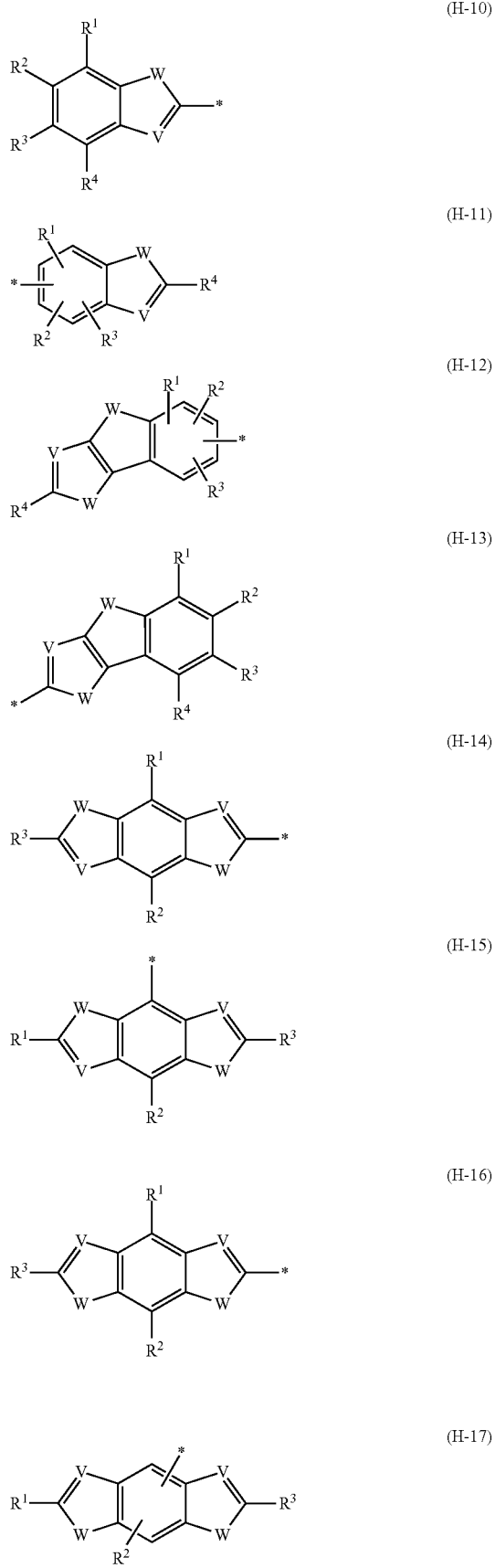

(H-18)
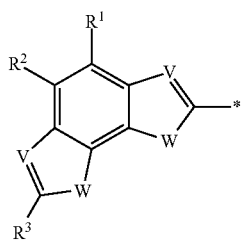
(H-19)
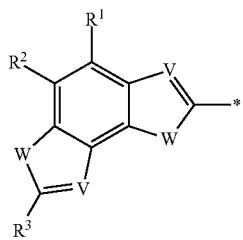
(H-20)
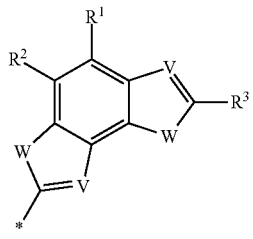
(H-21)
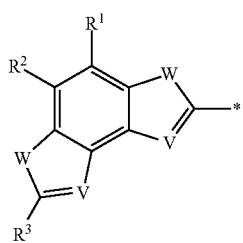
(H-22)
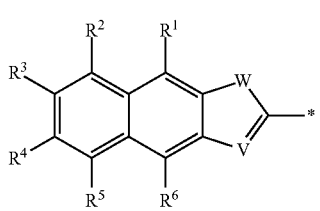
(H-23)
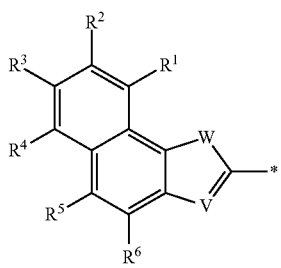
(H-24)
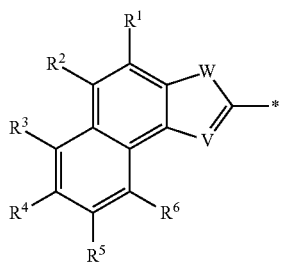
(H-25)
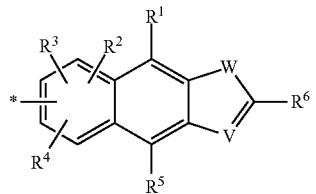
(H-26)
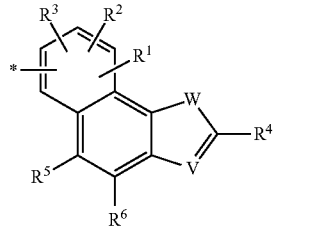
(H-27)
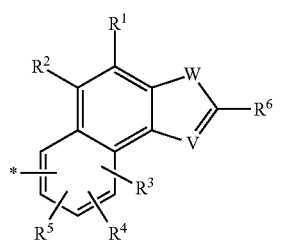
(H-28)
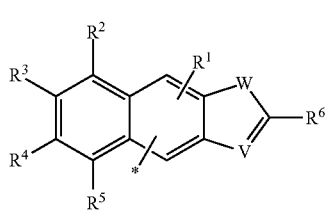
(H-29)
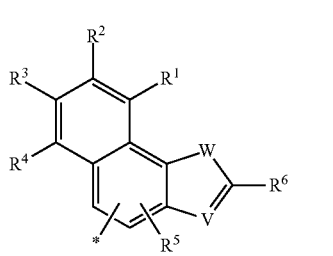

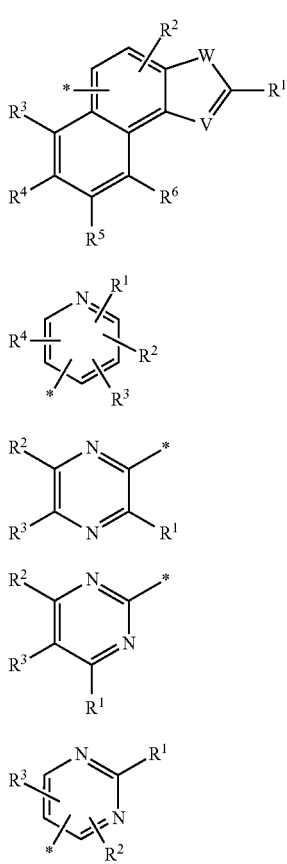

wherein
V is at each occurrence independently CR⁷ or N,
W is at each occurrence independently O, S or Se,
$R^1$, $R^2$, $R^3$, $R^4$, $R^5$, $R^6$ and $R^7$ are independently of each other H or $R^S$,
  wherein at least one of $R^1$, $R^2$, $R^3$, $R^4$, $R^5$, $R^6$ and $R^7$ present is $R^S$ so that each of formulae (H-1) to (H-34) is substituted with at least one $R^S$.

5. The compound according to claim 1, wherein a is not 0 and $Ar^5$ is at each occurrence independently arylene or heteroarylene having electron donor properties or arylene or heteroarylene having electron acceptor properties.

6. The compound according to claim 1, wherein a is 1.

7. The compound according to claim 1, which comprises at least two units M.

8. The compound according to claim 1, which is an oligomer or a polymer.

9. The compound according to claim 1, which is of formula (III-a)

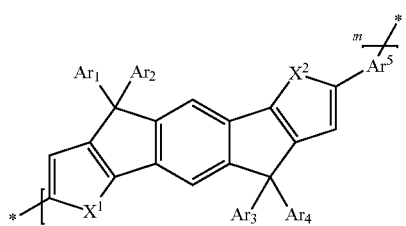

(III-a)

wherein m is at least 10.

10. A mixture or a blend comprising one or more compounds of claim 1 and one or more binders or compounds or polymers having semiconducting, charge transport, hole transport, electron transport, hole blocking, electron blocking, electrically conducting, photoconducting or light emitting properties.

11. A formulation comprising the compound of claim 1 and an organic solvent.

12. A charge transport, semiconducting, electrically conducting, photoconducting or light emitting material comprising the compound of claim 1 in said material.

13. A component or device comprising the compound of claim 1, said component or device being selected from the group consisting of organic field effect transistors (OFET), thin film transistors (TFT), integrated circuits (IC), logic circuits, capacitors, radio frequency identification (RFID) tags, radio frequency identification devices, radio frequency identification components, organic light emitting diodes (OLED), organic light emitting transistors (OLET), flat panel displays, backlights of displays, organic photovoltaic devices (OPV), organic solar cells (O-SC), photodiodes, laser diodes, photoconductors, organic photodetectors (OPD), electrophotographic devices, electrophotographic recording devices, organic memory devices, sensor devices, charge injection layers, charge transport layers in polymer light emitting diodes (PLEDs), interlayers in polymer light emitting diodes, Schottky diodes, planarising layers, antistatic films, polymer electrolyte membranes (PEM), conducting substrates, conducting patterns, electrode materials in batteries, alignment layers, biosensors, biochips, security markings, security devices, components for detecting and discriminating DNA sequences and devices for detecting and discriminating DNA sequences.

14. A component or device according to claim 13, which is selected from the group consisting of organic field effect transistors (OFET), thin film transistors (TFT), integrated circuitry (IC), radio frequency identification (RFID) tags, organic light emitting devices (OLED), organic light emitting transistors (OLET) and backlights of displays.

15. An optical, electrooptical, electronic, electroluminescent or photoluminescent component or device comprising a material according to claim 12.

16. The compound according to claim 1, wherein $R^S$ is at each occurrence independently alkyl having at least 5 and at most 40 carbon atoms.

17. The compound according to claim 1, wherein $R^S$ is at each occurrence independently alkyl having at least 10 and at most 40 carbon atoms.

18. The compound according to claim 1, wherein $R^S$ is at each occurrence independently alkyl having at least 15 and at most 40 carbon atoms.

19. The compound according to claim 4, wherein W is S.

20. The compound according to claim 4, wherein $R^S$ is at each occurrence independently alkyl having at least 15 and at most 40 carbon atoms.

* * * * *